(12) United States Patent
Schückler et al.

(10) Patent No.: US 9,737,488 B2
(45) Date of Patent: Aug. 22, 2017

(54) PHARMACEUTICAL COMPOSITION FOR THE TREATMENT OF CANCER

(75) Inventors: Fritz Schückler, Bergisch Gladbach (DE); Axel Wollenschläger, Bergisch Gladbach (DE)

(73) Assignee: Bayer HealthCare LLC, Whippany, NJ (US)

( * ) Notice: Subject to any disclaimer, the term of this patent is extended or adjusted under 35 U.S.C. 154(b) by 931 days.

(21) Appl. No.: 11/885,930

(22) PCT Filed: Feb. 22, 2006

(86) PCT No.: PCT/EP2006/001574
§ 371 (c)(1),
(2), (4) Date: Jun. 9, 2008

(87) PCT Pub. No.: WO2006/094626
PCT Pub. Date: Sep. 14, 2006

(65) Prior Publication Data
US 2008/0242707 A1    Oct. 2, 2008

Related U.S. Application Data

(60) Provisional application No. 60/658,827, filed on Mar. 7, 2005.

(51) Int. Cl.
*A61K 9/20* (2006.01)
*A61K 9/28* (2006.01)
*A61K 31/4412* (2006.01)

(52) U.S. Cl.
CPC .......... *A61K 9/2018* (2013.01); *A61K 9/2054* (2013.01); *A61K 9/284* (2013.01); *A61K 9/2813* (2013.01); *A61K 9/2866* (2013.01); *A61K 31/4412* (2013.01)

(58) Field of Classification Search
None
See application file for complete search history.

(56) References Cited

U.S. PATENT DOCUMENTS

| | | |
|---|---|---|
| 4,863,924 A | 9/1989 | Haga et al. |
| 4,910,022 A | 3/1990 | Bavitz et al. |
| 5,547,966 A | 8/1996 | Atwal et al. |
| 5,879,706 A | 3/1999 | Carter et al. |
| 6,106,865 A | 8/2000 | Staniforth et al. |
| 6,117,451 A | 9/2000 | Kumar |
| 6,187,799 B1 | 2/2001 | Wood et al. |
| 7,202,244 B2 | 4/2007 | Boyle et al. |
| 7,235,576 B1 | 6/2007 | Riedl et al. |
| 7,329,670 B1 | 2/2008 | Dumas et al. |
| 7,351,834 B1 | 4/2008 | Riedl et al. |
| 7,371,763 B2 | 5/2008 | Dumas et al. |
| 7,517,880 B2 | 4/2009 | Miller et al. |
| 7,528,255 B2 | 5/2009 | Riedl et al. |
| 7,557,129 B2 | 7/2009 | Scott et al. |
| 7,678,811 B2 | 3/2010 | Dumas et al. |
| 7,838,541 B2 | 11/2010 | Dumas et al. |
| 7,897,623 B2 | 3/2011 | Riedl et al. |
| 8,071,616 B2 | 12/2011 | Dumas et al. |
| 8,076,488 B2 | 12/2011 | Dumas et al. |
| 8,101,773 B2 | 1/2012 | Smith et al. |
| 8,110,587 B2 | 2/2012 | Dumas et al. |
| 8,124,630 B2 | 2/2012 | Riedl et al. |
| 8,124,782 B2 | 2/2012 | Logers et al. |
| 8,207,166 B2 | 6/2012 | Lee et al. |
| 8,242,147 B2 | 8/2012 | Dumas et al. |
| 8,618,141 B2 | 12/2013 | Dumas et al. |
| 8,637,553 B2 | 1/2014 | Boyer et al. |
| 8,680,124 B2 | 3/2014 | Wilhelm et al. |
| 8,748,622 B2 | 6/2014 | Stiehl et al. |
| 8,796,250 B2 | 8/2014 | Wilhelm et al. |
| 8,841,330 B2 | 9/2014 | Riedl et al. |
| 8,877,933 B2 | 11/2014 | Grunnenberg et al. |
| 9,181,188 B2 | 11/2015 | Dumas et al. |
| 2001/0006975 A1 | 7/2001 | Wood et al. |
| 2001/0011135 A1 | 8/2001 | Riedl et al. |
| 2001/0011136 A1 | 8/2001 | Riedl et al. |
| 2001/0014352 A1 | 8/2001 | Batra et al. |
| 2001/0016659 A1 | 8/2001 | Riedl et al. |
| 2001/0027202 A1 | 10/2001 | Riedl et al. |
| 2001/0034447 A1 | 10/2001 | Riedl et al. |
| 2002/0042517 A1 | 4/2002 | Uday et al. |
| 2002/0065296 A1 | 5/2002 | Dumas et al. |

(Continued)

FOREIGN PATENT DOCUMENTS

| | | |
|---|---|---|
| EP | 1056725 A1 | 12/2000 |
| EP | 04023130.0 | 9/2004 |

(Continued)

OTHER PUBLICATIONS

Rasenack et al., Int. J. Pharm., 2003, 254, pp. 137-145.*
Remington's Pharmaceutical Sciences, 17th Edition, 1985, Chapter 90, pp. 1603-1632.*
International Search Report dated Jul. 12, 2006 for PCT/EP2006/001574.
Wilhelm, Scott M. et al., "Bay 43-9006 Exhibits Broad Spectrum Oral Antitumor Activity and Targets the RAF/MEK/ERK Pathway and Receptor Tyrosine Kinase Involved in Tumor Progression and Angiogenesis," Cancer Research, Oct. 1, 2004, vol. 64, pp. 7099-7109.
Ahmad, Tanya et al., "Kinase Inhibition with BAY 43-9006 in Renal Cell Carcinoma," Clinical Cancer Research, Sep. 15, 2004, vol. 10, pp. 6388-6392.

(Continued)

*Primary Examiner* — Brian Gulledge
(74) *Attorney, Agent, or Firm* — Millen White Zelano & Branigan, P.C.

(57) ABSTRACT

The present invention pertains to a pharmaceutical composition comprising the compound of the formula (I) in a high concentration and at least one pharmaceutically acceptable excipient, the use of the composition for the treatment of hyper-proliferative diseases, such as cancer, either as a sole agent, or in combination with other anti-cancer therapies, and the process for preparing of said composition.

103 Claims, No Drawings

(56) References Cited

U.S. PATENT DOCUMENTS

| | | |
|---|---|---|
| 2002/0071857 A1* | 6/2002 | Kararli et al. ............... 424/435 |
| 2002/0137774 A1 | 9/2002 | Riedl et al. |
| 2002/0165394 A1 | 11/2002 | Dumas et al. |
| 2003/0105091 A1 | 6/2003 | Riedl et al. |
| 2003/0125359 A1* | 7/2003 | Lyons et al. ................. 514/350 |
| 2003/0139605 A1 | 7/2003 | Riedl et al. |
| 2003/0144278 A1 | 7/2003 | Riedl et al. |
| 2003/0181442 A1 | 9/2003 | Riedl et al. |
| 2003/0207870 A1 | 11/2003 | Dumas et al. |
| 2003/0207872 A1 | 11/2003 | Reidl et al. |
| 2003/0207914 A1 | 11/2003 | Dumas et al. |
| 2003/0216396 A1 | 11/2003 | Dumas et al. |
| 2003/0216446 A1 | 11/2003 | Dumas et al. |
| 2003/0232765 A1 | 12/2003 | Carter et al. |
| 2004/0023961 A1 | 2/2004 | Dumas et al. |
| 2004/0197256 A1 | 10/2004 | Rogers et al. |
| 2004/0209905 A1 | 10/2004 | Kubo et al. |
| 2004/0229937 A1* | 11/2004 | Dumas et al. ................. 514/452 |
| 2004/0235829 A1 | 11/2004 | Scott et al. |
| 2005/0032798 A1 | 2/2005 | Boyer et al. |
| 2005/0038031 A1 | 2/2005 | Dumas et al. |
| 2005/0038080 A1* | 2/2005 | Boyer et al. ................. 514/350 |
| 2005/0059703 A1 | 3/2005 | Wilhelm et al. |
| 2005/0256174 A1 | 11/2005 | Wood et al. |
| 2006/0058358 A1 | 3/2006 | Dumas et al. |
| 2006/0078617 A1 | 4/2006 | Schueckler |
| 2006/0247186 A1 | 11/2006 | Carter et al. |
| 2007/0020704 A1 | 1/2007 | Wilhelm et al. |
| 2007/0105142 A1 | 5/2007 | Wilhelm |
| 2007/0178494 A1 | 8/2007 | Elting et al. |
| 2007/0244120 A1 | 10/2007 | Dumas et al. |
| 2007/0265315 A1 | 11/2007 | Dumas et al. |
| 2008/0009527 A1 | 1/2008 | Dumas et al. |
| 2008/0027061 A1 | 1/2008 | Riedl et al. |
| 2008/0032979 A1 | 2/2008 | Riedl et al. |
| 2008/0085902 A1 | 4/2008 | Bold et al. |
| 2008/0108672 A1 | 5/2008 | Riedl et al. |
| 2008/0153823 A1 | 6/2008 | Riedl et al. |
| 2008/0194580 A1 | 8/2008 | Dumas et al. |
| 2008/0214545 A1 | 9/2008 | Lee et al. |
| 2008/0227828 A1 | 9/2008 | Dumas et al. |
| 2008/0242707 A1 | 10/2008 | Schuckler et al. |
| 2008/0269265 A1 | 10/2008 | Miller et al. |
| 2008/0300281 A1 | 12/2008 | Dumas et al. |
| 2008/0311601 A1 | 12/2008 | Elting et al. |
| 2008/0311604 A1 | 12/2008 | Elting et al. |
| 2009/0068146 A1 | 3/2009 | Wilhelm |
| 2009/0093526 A1 | 4/2009 | Miller et al. |
| 2009/0118268 A1 | 5/2009 | Riedl et al. |
| 2009/0192127 A1 | 7/2009 | Scheuring et al. |
| 2009/0215835 A1 | 8/2009 | Wilhelm et al. |
| 2009/0221010 A1 | 9/2009 | Elting et al. |
| 2009/0227637 A1 | 9/2009 | Weber et al. |
| 2009/0306020 A1 | 12/2009 | Scheuring et al. |
| 2010/0063088 A1 | 3/2010 | Wood et al. |
| 2010/0144749 A1 | 6/2010 | Wilhelm et al. |
| 2012/0040925 A1 | 2/2012 | Carter et al. |
| 2012/0142742 A1 | 6/2012 | Riedl et al. |
| 2012/0270878 A1 | 10/2012 | Miller et al. |
| 2014/0235678 A1 | 8/2014 | Bottger et al. |
| 2014/0329866 A1 | 11/2014 | Riedl et al. |
| 2014/0336210 A1 | 11/2014 | Carter et al. |
| 2016/0015697 A1 | 1/2016 | Dumas et al. |

FOREIGN PATENT DOCUMENTS

| | | |
|---|---|---|
| EP | 04023131.8 | 9/2004 |
| EP | 1 868 579 | 12/2007 |
| WO | 96/40673 A1 | 12/1996 |
| WO | 97/04765 A1 | 2/1997 |
| WO | 97/40028 A1 | 10/1997 |
| WO | WO-97 40028 | 10/1997 |
| WO | WO 98/52558 A1 | 11/1998 |
| WO | WO 98/52559 A1 | 11/1998 |
| WO | 99/32106 A1 | 7/1999 |
| WO | 9932436 A1 | 7/1999 |
| WO | WO 99/32106 A1 | 7/1999 |
| WO | WO 99/32110 A1 | 7/1999 |
| WO | WO 99/32111 A1 | 7/1999 |
| WO | WO 99/32436 A1 | 7/1999 |
| WO | WO 99/32455 A1 | 7/1999 |
| WO | WO 99/32463 A1 | 7/1999 |
| WO | 00/42012 A1 | 7/2000 |
| WO | WO 00/41698 A1 | 7/2000 |
| WO | WO-00 42012 | 7/2000 |
| WO | WO 00/42012 A1 | 7/2000 |
| WO | WO 02/062763 A2 | 8/2002 |
| WO | WO 02/076977 A2 | 10/2002 |
| WO | WO 02/085857 A2 | 10/2002 |
| WO | WO 02/085859 A1 | 10/2002 |
| WO | WO 03/004513 A1 | 1/2003 |
| WO | 03/047579 A1 | 6/2003 |
| WO | WO 03/047523 A2 | 6/2003 |
| WO | WO-03 047579 | 6/2003 |
| WO | WO 03/047579 * | 6/2003 |
| WO | WO 03/047579 A1 | 6/2003 |
| WO | 03/068228 A1 | 8/2003 |
| WO | WO 03/068223 A1 | 8/2003 |
| WO | WO-03 068228 | 8/2003 |
| WO | WO 03/068228 A1 | 8/2003 |
| WO | WO 03/068229 A1 | 8/2003 |
| WO | WO 03/068746 A1 | 8/2003 |
| WO | WO-03 090720 | 11/2003 |
| WO | WO 2004/078128 A2 | 9/2004 |
| WO | WO 2004/078746 A2 | 9/2004 |
| WO | WO 2004/078747 A1 | 9/2004 |
| WO | WO 2004/078748 A2 | 9/2004 |
| WO | WO 2004/113274 A2 | 12/2004 |
| WO | 2005/000284 A2 | 1/2005 |
| WO | WO-2005 000284 | 1/2005 |
| WO | WO 2005/000284 A2 | 1/2005 |
| WO | WO-2005 009367 | 2/2005 |
| WO | WO 2005/009961 A2 | 2/2005 |
| WO | 2005009367 | 3/2005 |
| WO | WO 2005/059179 A1 | 6/2005 |
| WO | WO 2005/110994 A2 | 11/2005 |
| WO | 2006/000914 A1 | 1/2006 |
| WO | WO 2006/026500 A1 | 3/2006 |
| WO | WO 2006/026501 A1 | 3/2006 |
| WO | 2006/034797 A1 | 4/2006 |
| WO | WO 2006/034796 A1 | 4/2006 |
| WO | WO 2006/034797 A1 | 4/2006 |
| WO | WO-2006 094626 | 9/2006 |
| WO | WO 2006/094626 A1 | 9/2006 |
| WO | WO 2006/125540 A1 | 11/2006 |
| WO | WO 2007/015947 A2 | 2/2007 |
| WO | WO 2007/047955 A2 | 4/2007 |
| WO | WO 2007/053573 A2 | 5/2007 |
| WO | WO 2007/054215 A1 | 5/2007 |
| WO | WO 2007/056011 A2 | 5/2007 |
| WO | WO 2007/056012 A2 | 5/2007 |
| WO | WO 2007/059094 A2 | 5/2007 |
| WO | WO 2007/059154 A2 | 5/2007 |
| WO | WO 2007/059155 A1 | 5/2007 |
| WO | WO 2007/064872 A2 | 6/2007 |
| WO | 2013/023970 A1 | 2/2013 |

OTHER PUBLICATIONS

Kramer, Boris W. et al., "Use of mitogenic cascade blockers for treatment of C-Raf induced lung adenoma in vivo: Cl-1040 strongly reduces growth and improves lung structure," BMC Cancer, Jun. 1, 2004, vol. 4, No. 24, pp. 1-6.

Wilhelm, et al., "BAY 43-9006 exhibits broad spectrum oral anti-tumor activity and targets the RAF/MEK/ERK pathway and receptor tyrosine kinases involved in tumor progression and antiogenesis", Cancer Research vol. 64, No. 19, Oct. 1, 2004, p. 7100.

Ahmad, et al., "Kinase inhibition with BAY 43-9006 in renal cell carcinoma", Clinical Cancer Research vol. 10, No. 18 pt. 2, Mar. 19, 2004, pp. 6388S-6392S.

(56) References Cited

OTHER PUBLICATIONS

Kramer, et al., "Use of mitogenic cascade blockers for treatment of C-Raf induced lung adenoma in vivo: Cl-1040 strongly reduces growth and improves lung structure.", BMC Cancer vol. 4, Jun. 1, 2004, p. 24.
Lowinger, Timothy B., et al., "Design and Discovery of Small Molecules Targeting Raf-1 Kinase," Current Pharmaceutical Design, 2002, 8, 2269-2278.
Lowinger, Timothy B., et al., "Discovery of a Novel Class of Potent Raf Kinase Inhibitors: Structure Activity Relationships," Clinical Cancer Research, vol. 6, Nov. 2000 (Supplement)—Proceedings of the 2000 NCI-EORTC-AACR Symposium.
Lyons, J.F., et al., "Discovery of a Novel Raf Kinase Inhibitor," Endocrine-Related Cancer (2001) 8, 219-225.
Smith, Roger A., et al., "Discovery of Heterocyclic Ureas as a New Class of Rat Kinase Inhhibitors: Identification of a Second Generation Lead by a Combinatorial Chemistry Approach," Bioorganic & Medicinal Chemistry Letters 11 (2001) 2775-2778.
Ahmad, T. et al., "Kinase inhibition with BAY 43-9006 in renal cell carcinoma," Clinical Cancer Research, Sep. 15, 2004, vol. 10, pp. 6388-6392.
Hotte, S. J. et al., "BAY 43-9006: Early Clinical Data in Patients with Advanced Solid Malignancies," Current Pharmaceutical Design, 2002, vol. 8, pp. 2249-2253.
Rasenack, N. et al., "Microcrystals for dissolution rate enhancement of poorly water-soluble drugs," International Journal of Pharmaceutics, 2003, vol. 254, pp. 137-145.
Sorbera, L. A. et al., "Bay-43-9006," Drugs of the Future, 2002, vol. 27, No. 12, pp. 1141-1147.
Bianchi et al., "A Phase II multi-center uncontrolled trial of sorafenib (BAY 43-9006) in patients with metastatic breast cancer" Journal of Clinical Oncology, Draft 33 pages (presented previously Oct. 30-Nov. 3, 2005).
Carlomagno et al.. "BAY 43-9006 Inhibition of Oncogenic RET Mutants," Journal of the National Cancer Institute, 2006, vol. 98, No. 5, pp. 326-334.
Carney et al., "Monitoring the Circulating Levels of the HER2/neu Oncoprotein in Breast Cancer," Clin Breast Cancer 5(2): 105-116, (2004).
Carter et al., "Anti-Tumor Efficacy of the Orally Active Raf Kinase Inhibitor BAY 43-9006 in Human Tumor Xenograft Models," Proceedings of the American Association for Cancer Res., vol. 42: p. 923, Mar. 2001, Abstract #4954.
Carter et al., "Drug-Tumor Interactions" pp. 362-365, in: Chemotherapy of Cancer, Second Edition, John Wiley & Sons, NY (1981).
Carter et al., "Sorafenib is efficacious and tolerated in combination with cytotoxic or cytostatic agents in preclinical models of human non-small cell lung carcinoma," Cancer Chemotherapy and Pharmacology, Springer Berlin/Heidelberg, vol. 59, No. 2, pp. 183-195 (Feb. 2007). Abstract.
Chang et al., "BAY 43-9006 (Sorafenib) inhibits ectopic (s.c.) and orthotopic growth of a murine model of renal adenocarcinoma (Renca) predominantly through inhibition of tumor angiogenesis," 96th Annual Meeting, Anaheim/Orange County, CA, Apr. 16-20, 2005, 1 page.
Chang et al., "Sorafenib (BAY 43-9006) inhibits tumor growth and vascularization and induces tumor apoptosis and hypoxia in RCC xenograft models," Cancer Chernother. Pharmacol., 2007, vol. 59, pp. 561-574.
Clark et al., "Safety and Pharmacokinetics of the Dual Action Raf Kinase and Vascular Endothelial Growth Factor Receptor Inhibitor, BAY 43-9006, in Patients with Advanced, Refractory Solid Tumors," Clinical Cancer Res., Aug. 1, 2005, vol. 11, No. 15, pp. 5472-5480.
DeGrendele, "Activity of the Raf Kinase Inhibitor BAY 43-9006 in Patients with Advanced Solid Tumors," Clinical Colorectal Cancer, May 2003, vol. 3, pp. 16-18.
Dumas et al.. "Recent developments in the discovery of protein kinase inhibitors from the urea class," Current Opinion in Drug Discovery & Development, 2004, vol. 7, No. 5. pp. 600-616.

Dumas et al., "Synthesis and Pharmacological Characterization of a Potent, Orally Active p38 Kinase Inhibitor," Bioorganic & Medicinal Chemistry Letters, 2002, vol. 12, pp. 1559-1562.
Eisen et al., "Phase I trial of BAY 43-9006 (Sorafenib) combined with dacarbazine (DTIC) in metastatic melanoma patients," Abstract #7508, Meeting: 2005 ASCO Annual Meeting, Category: Melamona, Subcategory: Melamona.
Eisen et al., "Sorafenib in advanced melanoma: a Phase II randomised discontinuation trial analysis" British Journal of Cancer 95, 581-586 (2006).
Elting et al., "Biomarkers associated with clinical outcomes in TARGETs, a Phase III single-agent, placebo-controlled study of sorafenib in advanced renal cell carcinoma," Proc. Amer. Assoc. Cancer Res. vol. 47, Abstract # 2909, 2006, pp. 683-684.
Escudier et al., "Randomized Phase III trial of the Raf kinase and VEGFR inhibitor sorafenib (BAY 43-9006) in patients with advanced renal cell carcinoma (RCC)," Meeting: 2005 ASCO Annual Meeting, Category: Genitourinary Cancer, Subcategory: Kidney Cancer, 1 page.
Escudier et al., "Sorafenib in Advanced Clear-Cell Renal-Cell Carcinoma" New England Journal of Medicine vol. 356: 125-134 (Jan. 11, 2007).
Flaherty et al., "A Phase I Trial of the Oral, Multikinase Inhibitor Sorafenib in Combination vith Carboplatin and Paclitaxel" Clin Cancer Res 41(15):4836-4842 (Aug. 1, 2008).
Flaherty et. al., "Phase I/II trial of Bay 43-9006 carboplatin (C) and paclitaxel (P) demonstrates preliminary antitumor activity in the expansion cohort of patients with metastatic melanoma." Journal of Clinical Oncology, 2004 ASCO annual meeting proceedings, vol. 22, No. 14S (2004) Supplement: 7507, 4 pages.
Abou-Alfa et al., "Phase II Study of Sorafenib in Patients With Advanced Hepatocellular Carcinoma" Journal of Clinical Oncology, vol. 24, No. 26, pp. 4293-4300 (Sep. 10, 2006).
Gollob, "Sorafenib: scientific rationales for single-agent and combination therapy in clear-cell renal cell carcinoma" Pub Med PMID: 16425993, Clin. Genitourin. Cancer 4(3):167-174 (2005) abstract.
Gridelli et al., "Sorafenib and Sunitinib in the Treatment of Advanced Non-Small Cell Lung Cancer" The Oncologist (2007) 12:191-200.
Gupta et al., "Sorafenib targets BRAF and VEGFR in metastatic thyroid carcinoma" Journal of Clinical Oncology, 2007 ASCO Annual Meeting Proceedings (Post-Meeting Edition) vol. 25, No. 18S (Jun. 20 Supplement), 2007: 6019 abstract.
Hahn et al., "Sorafenib," Curr. Opin. Oncol. 18:615-621 (2006).
Heim et al., "Antitumor effect and potentiation or reduction in cytotoxic drug activity in human colon carcinoma cells by the Raf kinase inhibitor (RKI) BAY 43-9006," International Journal of Clinical Pharmacology and Therapeutics, 2003, vol. 41, No. 12, pp. 616-617.
Heim et al., "The Raf kinase inhibitor BAY 43-9006 reduces cellular uptake of platinum compounds and ctotoxity in human colorectal carcinoma cell lines," Anti-Cancer Drugs, 2005, vol. 16, pp. 129-136.
Hilger et al., "Correlation of ERK-phosphorylation and toxicities in patients treated with the Raf kinase inhibitor BAY 43-9006" International Journal of Clinical Pharmacology and Therapeutics, vol. 42, No. 11, pp. 648-649 (2004).
Hilger et al., "ERK1/2 phosphorylation: a biomarker analysis within a phase I study with the new Raf kinase inhibitor Bay 43-9006" International Journal of Clinical Pharmacology and Therapeutics, vol. 40, No. 12, pp. 567-568 (2002).
Hilger et al., "Inhibition of ERK phosphorylation and clinical outcome in patients treated with the Raf kinase inhibitor BAY 43-9006" Proc Am Soc Clin Oncol 21: 2002 (abstr 1916), 3 pages.
Hotte et al., "Bay 43-9006: Early clinical data in patients with advanced solid malignancies," Current Pharmaceutical Design, 8: 2249-2253, 2002.
Jain et al., "Randomized Discontinuation Trial of Sorafenib (BAY 43-9006)," Cancer Biology & Therapy, vol. 5, Issue 10, pp. 1270-1272 (2006).
Khire et al., "Omega-carboxypyridyl substituted ureas as Raf kinase inhibitors: SAR of the amide substituent," Bioorg. Med. Chem. Lett., 2004, vol. 14, pp. 783-786.

(56) References Cited

OTHER PUBLICATIONS

Kupsch et al., "Results of a Phase I Trial of Sorafenib (BAY 43-9006) in Combination with Oxaliplatin in Patients with Refractory Solid Tumors, including Colorectal Cancer," Clinical Colorectal Cancer, Cancer Information Group Journal, vol. 5 Issue 3, pp. 188-196, abstract (Sep. 2005).
Lee et al., "BAY-43-9006 Bayer/Onyx," Current Opinion in Investigational Drugs, 2003, vol. 4, No. 6, pp. 757-763.
Lorigan et al., "Phase II trial of sorafenib combined with dacarbazine in metastatic melanoma patients" ASCO 2006 DTIC abstract, 2 pages (Jan. 11, 2006).
Lyons et al., "Discovery of a novel Raf kinase inhibitor." *Endocrine-Related Cancer*, 2001, vol. 8, pp. 219-225.
Madwed et al., "Pharmacological evaluation of BIRB 796, a selective inhibitor of p38 MAP kinase (MAPK), in animal models of endotoxic shock, inflammation and arthritis," Inflammation Res., 50:S184, abstract No. W22/03, 2001.
Magnuson et al., "The Raf-1 serine/threonine protein kinase," Cancer Biology, vol. 5, 1994, pp. 247-253.
Manenti et al., "Circulating plasma vascular endothelial growth factor in mice hearing human ovarian carcinoma xengraft correlates with tumor progression and response to therapy," Molecular Cancer Therapeutics, 4(5): 715-725 (May 2005).
Mannová et al., "Activation of the N-Ras-PI3K-Akt-mTOR Pathway by Hepatitis C Virus: Control of Cell Survival and Viral Replication," Journal of Virology, Jul. 2005, vol. 79, No. 14, pp. 8742-8749.
Markgraf et al., "Strained Heterocyclic Systems. 19. 1-Azatriptycene and Derivatives," Tetrahedron, vol. 47, No. 2. 1991, pp. 183-188.
Marshall, "MAP kinase kinase kinase, MAP kinase kinase, and MAP kinase," Curr. Opin, Genet. Dev. 4: 82-89, 1994.
Marx, J., "Why a New Cancer Drug Works Well, in Some Patients." Science, vol. 304, p. 658-659, 2004.
McGoon et al., "Screening, Early Detection, and Diagnosis of Pulmonary Arterial Hypertension," CHEST, 2004: 126, pp. 14S-34S.
Medinger et al., "Hemmung der Tumorangiogenese Neue Therapieoptionen in der Onkologie,"Med Welt, 2006, 57, pp. 437-441.
Med Report Deutschland, "Sorafenib zur Therapie des fortgeschrittenen Nierenzellkarzinoms zugelassen," (2006), 1 page.
Meuillet et al , "In Vivo Molecular Pharmacology and Antitumor Activity of the Targeted Akt Inhibitor PX-316," Oncology vol. 14, 2004, pp. 513-527.
Michaelis, "Phenylharnstoff des 1-Phenyl-3-methyl-5-aminopyrazols,"justus Liebigs Ann, Chem. (JLACBF) 397, 1913, p. 143.
Milanini et al.. "p42/p44 MAP Kinase Module Plays a Key Role in the Transcriptional Regulation of the Vascular Endothelial Growth Factor Gene in Fibroblasts," Journal of Biological Chemistry, 27:3(29):18165-18172 (Jul. 17, 1998).
Milano et al., "New molecular targeted therapies in thyroid cancer" Anti-Cancer Drugs (2006) © Lippincott Williams & Wilkins., vol. 17:869-879.
Mills et al., "The Effects of Standard Anthracycline-Based Chemotherapy on Soluble ICAM-1 and Vascular Endothelial Growth Factor Levels in Breast Cancer," Clinical Cancer Research, 10: 4998-5003 (Aug. 1, 2004).
Milojokovic et al., "Immunohistochemical Characterisation of Vascular Endothelial Growth Factor (VEGF) and its Receptors Flt-1 and KDR in Chronic Myeloid Leukaemia (CML) Patients Treated with Imatinib Mesylate," Blood, 104 Abstract 1999 (2004).
Minna et al., "A Bull's Eye for Targeted Lung Cancer Therapy," Science, vol. 304, pp. 1458-1460, 2004.
Molhoek et al., "Synergistic inhibition of human melanoma proliferation by combination treatment with B-Raf inhibitor BAY 43-9006 and mTOR inhibitor rapamyein," Journal of Translational Medicine (2005) 3:39, pp. 1-11.
Motzer et al., "Survival and Prognostic Stratification of 670 Patients With Advanced Renal Cell Carcinoma", J. Clin. Oncol., 17(8):pp. 2530-2540 (1999).
Mross et al., "Drug-drug interaction pharmacokinetic study with the Raf kinase inhibitor (RKI) BAY 43-9006 administered in combination with irinotecan (CPT-11) in patients with solid tumors," International Journal of Clinical Pharmacology and Therapeutics, 2003, vol. 41, No. 12, pp. 618-619.
Mross et al., "Results from an an vitro and a clinical/pharmacological phase I study with the combination irinotecan and sorafenib" European Journal of Cancer 43, pp. 55-63 (2007).
Murphy et al., "BAY 43-9006 controls tumor growth through inhibition of vascular development," 96th Annual Meeting, Anaheim/Orange County, CA, Apr. 16-20, 2005, abstract No. 2985.
National Cancer Institute. "Carboplatin and Paclitaxel With or Without Sorafenib in Treating Patients With Unresectable Stage III or Stage IV Melanoma", 7 pages, NCT00110019, clinicaltrials.gov. (2005).
National Institutes of Health Clinical Center, "BAY 43-9006 (Sorafenib) to Treat Relapsed Non-Small Cell Lung Cancer", 4 pages, NCT00098254, clinicaltrials.gov (2005).
Panka et al., "BAY 43-9006 induces apoptosis in melanoma cell lines," 96th Annual Meeting, Anaheim/Orange County, CA, Apr. 16-20, 2005, abstract No. 5328.
Robert et al., "Phase I trial of sorafenib (BAY 43-9006) in combination with interferon alpha-2a in patients with unresectable and/or metastatic renal cell carcinoma and malignant melanoma," European Journal of Cancer, 2005, vol. 3, No. 2, p. 254, Abstract 883.
Rahmani et al., "Apoptosis Induced by the Kinase Inhibitor BAY 43-9006 in Human Leukemia Cells Involves Down-regulation of Mcl-1 through Inhibition of Translation," J. Biol. Chem, 280(42):35217-35227 (2005).
Ratain et al.. "Phase II Placebo-Controlled Randomized Discontinuation Trial of Sorafenib in Patients with Metastatic Renal Cell Carcinoma," Journal of Clinical Oncology vol. 24 No. 16, pp. 2505-2512 (Jun. 1, 2006).
Reddy et al., "Sorafenib: recent update on activity as a single agent and in combination with interferon-alpha2 in patients with advanced-stage renal cell carcinoma," Clin. Genitourin. Cancer 4:246-248 (2006) abstract.
Richly et al., "A phase I clinical and pharmacokinetic study of the Raf kinase inhibitor (RKI) BAY 43-9006 administered in combination with doxorubicin in patients with solid tumors," International Journal of Clinical Pharmacology and Therapeutics, 2003, vol. 41, No. 12, pp. 620-621.
Richly et al., "Results of a Phase I trial of sorafenib (BAY 43-9006) in combination with doxorubicin in patients with refractory solid tumors," Annals of Oncology, 2006, 17, pp. 866-873.
Richly et al., "Results of a phase I trial of BAY 43-9006 in combination with doxorubicin in patients with primary hepatic cancer," International Journal of Clinical Pharmacology and Therapeutics, 2004, vol. 42, No. 11, pp. 650-651.
Siu et al., "Phase I study of oral raf-1 kinase inhibitor BAY 43-9006 with gemcitabine in patients with advanced solid tumors," Abstract No. 828, Proc. Am. Soc. Clin. Oncol., 2003, vol. 22, p. 207.
Siu et al., "Phase I Trial of Sorafenib and Gemcitabine in Advanced Solid Tumors with an Expanded Cohort in Advanced Pancreatic Cancer," Clin. Cancer Res. 12(1):144-151 (2006).
Smith et al., (Abstract) "Recent Advances in the Research and Development of RAF Kinase Inhibitors," Current Topics in Medicinal Chemistry 6(11):1071-1089 (2006).
Sorbara et al. "BAY 43-9006," Drugs of the Future, 2002, vol. 27, No. 12, pp. 1141-1147.
Strumberg, D., "Preclinical and Clinical Development of the Oral Multikinase Inhibitor Sorafenib in Cancer Treatment," Drugs of Today, 41(12): 773-784 (2005).
Strumberg et al., "Phase I Clinical and Pharmacokinetic Study of the Novel Raf Kinase and Vascular Endothelial Growth Factor Receptor Inhibitor BAY 43-9006 in Patients With Advanced Refractory Solid Tumors," Journal of Clinical Oncology, Feb. 10, 2005, vol. 23, No. 5, pp. 965-972.

(56) References Cited

OTHER PUBLICATIONS

Strumberg et al., "Phase I Clinical, Pharmacokinetic and Pharmacodynamic Study of the Raf Kinase Inhibitor BAY 43-9006 in Patients with Locally Advanced or Metastatic Cancer," Proc. Am. Soc. Clin. Oncol. 20: 2001 (abstr 330).

Strumberg et al., "Results of phase I pharmacokinetic and pharmacodynamic studies of the Raf kinase inhibitor BAY 43-9006 in patients with solid tumors," International Journal of Clinical Pharmacology and Therapeutics, 2002, vol. 40, No. 12, pp. 580-581.

Tong et al., "Pharmacodynamic Monitoring of BAY 43-9006 (Sorafenib) in Phase I Clinical Trials Involving Solid Tumor and AML/MDS Patients, Using Flow Cytometry to Monitor Activation of the ERK Pathway in Peripheral Blood Cells," Cytometry Part B (Clinical Cytometry) 70B: 107-114 (2006).

Gupta-Abramson et al., "Phase II Trial of Sorafenib in Advanced Thyroid Cancer" Journal of Clinical Oncology vol. 26, No. 29, pp. 4714-4719 (Oct. 10, 2008).

Veronese et al., "Mechanisms of Hypertension Associated with BAY 43-9006," Journal of Clinical Oncology, 2006, vol. 24, No. 9, pp. 1363-1369.

Wakelee et al., "Targeting Angiogenesis with Vascular Endothelial Growth Factor Receptor Small-Molecular Inhibitors: Novel Agents with Potential in Lung Cancer," Clinical Lung Cancer, 7(Suppl 1): S31-538 (Sep. 2005).

Wald et al., "Involvement of the CXCL12/CXCR4 pathway in the advanced liver disease that is associated with hepatitis C virus or hepatitis B virus," Eur J Immunol., vol. 34, p. 1164-1174 (2004).

Wan et al., "Mechanism of Activation of the RAF-ERK Signaling Pathway by Oncogenic Mutations of B-RAF" Cell, Mar. 19, 2004, vol. 116, pp. 855-867.

Weekly Epidemiological Record, "Influenza," World Health Organization. Apr. 1999; vol. 4, pp. 111-112.

Wermuth, C. G., "Designing Prodrugs and Bioprecursors II: Bioprecursor Prodrugs," in: The Practice of Medicinal Chemistry, Academic Press Limited 1996, pp. 697-715.

White et al., "Heterocyclic Ureas: Inhibitors of Acyl-CoA:Cholesterol O-Acyltransferase as Hypocholesterolemic Agents," J. Med. Chem, 1996, 39, pp. 4382-4395.

Wierzbowska et al., "Circulating VEGF and its soluble receptors sVEGFR-1 and sVEGFR-2 in patients with acute leukemia," Eur. Cytokine Netw., 14(3): 149-153 (Sep. 2003).

Wilhelm et al., "A Novel RAF Kinase Inhibitor Blocks the RAF/MEK/ERK Pathway in Tumor Cells," Poster, 92nd Annual Meeting of the American Association for Cancer Research, Mar. 24-28, 2001, New Orleans, LA USA, 1 page.

Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," Cancer Research, Oct. 1, 2004, vol. 64, pp. 7099-7109.

Wilhelm et al., "BAY 43-9006: Preclinical Data," Curr Pharm Des, 2002, vol. 8, No. 25, pp. 2255-2257.

Wilhelm et al., "Discovery and development of sorafenib: a multikinase inhibitor for treating cancer," Nature Reviews, Drug Discovery, 2006, vol. 5, pp. 835-844.

Wilhelm et al., "Preclinical overview of sorafenib, a multikinase inhibitor that targets both Raf and VEGF and PDGF receptor tyrosine kinase signaling," Mol. Cancer Ther., 2008, vol. 7, No. 10, pp. 3129-3140.

Wilkinson Geoffrey, "Contents," 7 pages in: Comprehensive Organometallic Chemistry. The Synthesis, Reactions, and Structures of Organometallic Compounds, Pergamon Press, Oxford, U.K. 1982: vol. 1-3.

Wilson et al., "The structural basis for the specificity of pyridinylimidazole inhibitors of p38 MAP kinase," Chemistry & Biology, 1997, vol. 4, No. 6, pp. 423-431.

Stollorz, "Die Krebsformel, die der Zufall fand," Frankfurter Allgemeine Sonntagszeitung, Jul. 2, 2006, NR 26, pp. 68-69.

Wissner et al., "Analogues of Platelet Activating Factor. 7. Bis-Aryl Amide and Bis-Aryl Urea Receptor Antagonists of PAF," J. Med. Chem., 1992, vol. 35, pp, 4779-4789.

Wojnowski et al., "Endothelial apoptosis in Braf-deficient mice," Nature Genetics vol. 16, pp. 293-297 (Jul. 1997).

Onyx Pharmaceuticals, Inc.,"Novel RAF Kinase inhibitor BAY 43-9006 Shows Early Signs of Tolerability and Activity in Phase 1B Combination Trials Reported at ASCO," 1 page, (Press Release: Jun. 2, 2003).

Wright et al., "Clinical Trials Referral Resource. Current Clinical Trials of BAY 43-9006, Part 1," Oncology, Apr. 2005, vol. 19, No. 4: pp. 499-502.

Carter et al., "Anti-tumor Efficacy of the Orally Active RAF Kinase Inhibitor Bay 43-90006 in Human Tumor Xenograft Model," #4954, Proceedings of the American Association for Cancer Res., 2001, vol. 42, p. 923.

Riedl et al., # 4956 "Potent *Raf* Kinase Inhibitors from the Diphenylurea Class: Structure Activity Relationships," Proceedings of the American Association for Cancer Research, vol. 42, Mar. 2001, p. 923, 92nd Annual Meeting of the American Association for Cancer Research; New Orleans, LA, USA; Mar. 24-28, 2001.

Stromberg et al., abstract No. #2921 "Phase I and Pharmacokinetic Study of the Raf Kinase inhibitor Bay 43-9006 in Patients with Locally Advanced or Metastic Cancer," Proceedings of the American Association for Cancer Research, vol. 42, Mar. 2001, p. 543, 92nd Annual Meeting of the American Association for Cancer Research;New Orleans, LA, USA; Mar. 24-28, 2001.

Kurik et al., "Optical Properties of Segmented Oligourethane with Azomethine Terminal Fragments," Polymer Science, series B, 1996, vol. 38 pp. 2038-2041 English translation.

Michaelis, "Phenylharnstoff des 1-Phenyl-3-methyl-5-aminopyrazols," Justus Liebigs Ann. Chem. (JLACBF) 397, 1913, p. 143 English translation.

Peters, H.D., "Sorafenib bei soliden Tumoren," Focus Onkologie, 2007, Auflage 12000, 6 pages English translation.

Strumberg et al., "Sorafenib Neue Therapieoption in der Onkologie," Krankenhauspharmazie, 2007, vol. 28, pp. 93-97, pp. 1/5, 2/5, 3/5 and 4/5 English translation.

Stollorz, "Die Krebsformel, die der Zufall fand," Frankfurter Allgemeine Sonntagszeitung, Jul. 2, 2006, NR 26, pp. 68-69 English translation.

Ritschel, W. A. et al., Die Tablette, 2002, 2nd Completely Revised and Expanded Edition.

English Translation of Ritschel, W. A. et al., Die Tablette, 2002, 2nd Completely Revised and Expanded Edition.

S. Dawoodbhai et al., "The Effect of Moisture on Powder Flow and on Compaction and Physical Stability of Tablets", Drug Development and Industrial Pharmacy, vol. 15, No. 10 (1989) pp. 1577-1600.

R.C. Rowe et al., "Handbook of Pharmaceutical Excipients", Pharmaceutical Press, Fourth Edition (2003) pp. 249-251.

A.R. Gennaro, "Remington: The Science and Practice of Pharmacy", Publisher Lippincott Williams & Wilkins, vol. 1, 20th Edition (2000) pp. 224-248.

Priority Document for related Indian Application No. 1960/DELNP/2007, filed Mar. 14, 2007.

Strumberg et al. Phase I Clinical and Pharmacokinetic Study of the Novel Raf Kinase and Vascular Endothelial Growth Factor Receptor Inhibitor BAY 43/9006 in Patients With Advanced Refractory Solid Tumors, Journal of Clinical Oncology, vol. 23, No. 5, Feb. 10, 2005, pp. 965-972.

Under Seal—Notice of certification letter on behalf of Mylan Pharmaceuticals Inc. ("Mylan") marked "Confidential" to Bayer Healthcare LLC. ("Bayer"), the holder of approved New Drug Application ("NDA") No. 21923 Nexavar® tablets, based on U.S. Pat. No. 8,618,141.

John K. Buolamwini, "Novel Anticancer Drug Discovery," Curr. Opin. Chem. Biol. Aug. 1999, 3(4):500-09.

Rika Hoshino et al., "Constitutive activation of the 41-/43-kDa mitogen-activated protein kinase signaling pathway in human tumors," Oncogene Jan. 21, 1999, 18:813-22.

(56) References Cited

OTHER PUBLICATIONS

Khire, U. R. et al., Omega-carboxypyridyl substituted Ureas as Raf Kinase Inhibitors: SAR of the Amide Substituent, Bioorganic & Medicinal Chemistry Letters 14, pp. 783-786, (2004).
Wilhelm S. et al., Discovery and Development of Sorafenib: A Multikinase Inhibitor for Treating Cancer, Nature Reviews Drug Discovery 5, pp. 835-844, (2006).
Lipinski, C. A. et al., Experimental and Computational Approaches to Estimate Solubility and Permeability in Drug Discovery and Development Settings, Advanced Drug Delivery Reviews 23, pp. 3-25, (1997).
Curatolo, W., Physical Chemical Properties of Oral Drug Candidates in the Discovery and Exploratory Development Settings, PSTT vol. 1, No. 9, pp. 387-393, Dec. 1998.
J. Keith Guillory, "Generation of Polymorphs, Hydrates, Solvates, and Amorphous Solids" 183 in Polymorphism in Pharmaceutical Solids (H.G. Brittain Ed.) (1999).
Quinn et al., Phase II Trial of Temozolomide in Patients With Progressive Low-Grade Glioma; Journal of Clinical Oncology, vol. 21, No. 4 (Feb. 15) 2003: pp. 646-651.
Wood et al., PTK787/ZK 222584, a Novel and Potent Inhibitor of Vascular Endothelial Growth Factor Receptor Tyrosine Kinases, Impairs Vascular Endothelial Growth Factor-inducted Responses and Tumor Growth After Oral Administration; Cancer Research 60, pp. 2178-2189, Apr. 15, 2000.
Raymond et al., Epidermal Growth Factor Receptor Tyrosine Kinase as a Target for Anticancer Therapy, Review Article; Drugs 2000; 60 Suppl. 1: pp. 15-23.
Harari et al., Molecular Mechanisms Underlying ErbB2/HER2 Acton in Breast Cancer, Oncogene (2000) 19, pp. 6102-6114.
Baselga J., Drugs, Abstract, vol. 60, Supplement 1, 2000 pp. 33-40(8); Publisher Adis International.
Jani et al., Discovery and Development of CP-724714, a Selective HER2 Receptor Tyrosine Kinase Inhibitor; Abstract, Journal of Clinical Oncology, 2004 ASCO Annual Meeting Proceedings (Post-Meeting Edition), vol. 22, No. 14S (Jul. 15 Supplement), 2004; 3122.
Rabindran et al., Antimor Activity of HKI-272, An Orally Active, Irreversible Inhibitor of the HER-2 Tyrosine Kinase; Cancer Research 64, pp. 3958-3965, Jun. 1, 2004).
Demetri et al., SU11248, A Multi-targeted Tyrosine Kinase Inhibitor, Can Overcome Imatinib (IM) Resistance Caused By Diverse Genomic Mechanisms in Patients (PTS) With Metastatic Gastrointestinal Stromal Tumor (GIST); Journal of Clinical Oncology, 2004 ASCO Annual Meeting Proceedings (Post-Meeting Edition), vol. 22, No. 14S (Jul. 15, Supplemental), 2004: 3001.
Hennequin et al., 92nd AACR Meeting, Abstract, New Orleans, Mar. 24-28, 2001, vol. 42.
Herbst et al., Targeting the Epidermal Growth Factor Receptor in Non-Small Cell Lung Cancer; Clinical Research, Abstract, vol. 9, pp. 5813-5824, Dec. 1, 2003.
Taguchi et al., A Novel Orally Active Inhibitor of VEGF Receptor Tyrosine Kinases KRN951: Anti-angiogenic and Anti-tumor Activity Against Human Solid Tumors; Abstract, 95th AACR Meeting. 2002.
Beebe et al., Pharmacological Characterization of CP-547-632, A Novel Vascular Endothelial Growth Factor Receptor-2 Tyrosine Kinase Inhibitor for Cancer Therapy; Cancer Research 63, pp. 7301-7309, Nov. 1, 2003.
Roberts et al., Experimental and Molecular Therapeutics 38: Novel Therapeutic Agents III: Signaling Inhibitors Abstract #3989, Proceedings of the American Association of Cancer Research Abstract, vol. 45, 2004.
Lee et al., Experimental and Molecular Therapeutics 18: Pharmacogenomics, Preclinical Toxicology, Pharmacokinetics Abstract #2130, Proceedings of the American Cancer Research Abstract, vol. 45, 2004.
Chia-Rui Shen et al., Peptides Containing a Dominant T-cell Epitope from Red Cell Band 3 Have in Vivo Immunomodulatory Properties in NZB Mice with Autoimmune Hemolytic Anemia, Blood Journal Org. Abstract, 2003 102: pp. 3800-3806.
Hennequin et al., Experimental and Molecular Therapeutics 41: Antiangiogenesis Abstract #4539; Proceedings of the American Cancer Research, Abstract, vol. 45, 2004.
Avruch et al., Ras Activation of the Raf Kinase: Tyrosine Kinase Recruitment of the MAP Kinase Cascade, The Endocrine Society, Abstract, Nov. 23, 2010.
Lawlor et al., PKB/Akt: A Key Mediator of Cell Proliferation, Survival and Insulin Responses, Journal of Cell Science 114, pp. 2903-2910 (2001).
Sebolt-Leopold et al., Experimental and Molecular Therapeutics 39: Novel Therapeutic Agents IV: Small Molecule Inhibitors Abstract #4003, Proceedings of the American Cancer Research, Abstract, vol. 45, 2004.
Wallace et al., Experimental and Molecular Therapeutics 37: Signaling Targets Abstract #3891, Proceedings of the American Cancer Research, Abstract, vol. 45, 2004.
Ottmann et al., A Phase I, Pharmacokinetic (PK) and Pharmacodynamic (PD) Study of A Novel Histone Deacetylase Inhibitor LAQ824 in Patients with Hematologic Malignancies; Journal of Clinical Oncology, 2004 ASCO Meeting Proceedings (Post-Meeting Edition), Abstract, vol. 22, No. 14S (Jul. 15 Supplemental), 2004: 3024.
Beck et al., Phase I Pharmacokinetic (PK) and Pharmadocynamic (PD) Study of LBH589A: A Novel Histone Deacetylase Inhibitor, Journal of Clinical Oncology, 2004 (ASCO Annual Meeting Proceedings (Post-Meeting Edition), Abstract, vol. 22, ano. 14S (Jul. 15, Supplemental), 2004: 3025.
Ryan et al., Experimental Molecular Therapeutics 23: Histone Deacetylase Inhibitors Abstract #2452, Proceedings of the American Cancer Research, Abstract, vol. 45, 2004.
Piekarz et al., Update on the Phase II Trialand Correlative Studies of Depsipeptide in Patients with Cutaneous T-Cell Lymphoma and Relapsed Peripheral T-cell Lumphoma, Journal of Clinical Oncology, 2004 ASCO Annual Meeting Proceedings (Post-Meeting Edition), Abstract, vol. 22, No. 14S (Jul. 15 Supplemental), 2004: 3028.
Mackay et al., A Phase II Trial of the Proteosome Inhibitor PS-341 in Patients with Metastatic Colorectal Cancer, Journal of Clinical Oncology, 2004 ASCO Annual Meeting Proceedings (Post-Meeting Edition), Abstract, vol. 22, No. 14S (Jul. 15 Supplemental), 2004: 3109.
Wu et al., Experimental and Molecular Therapeutics 36: Signal Transduction Inhibitors Abstract #3849, Proceedings of the American Association Cancer Research, Abstract, vol. 45, 2004.
Green et al., Identification of Critical Domains and Putative Partners for the Caenorhabditis Elegans Spindle Component LIN-5; Mol. Gen Genomics Abstract, (2004) 271: pp. 532-544.
Wood et al., Past and Future of the Mitotic Spindle as an Oncology Target; Current Opinion in Pmarmacology 2001, pp. 370.377.
Pollack et al., Inhibition of Epidermal Growth Factor Receptor-Associated Tyrosine Phosphorylation in Human Darcinomas with CP-358,744: Dynamics of Receptor Inhibition In Situ and Antitumor Effects in Athymic Mice; The Journal of Pharmacology and Experimental Therapeutics, JPET 291; pp. 739-748, 1999.
Complaint dated Jan. 30, 2015—Bayer HealthCare LLC, *Bayer HealthCare Pharmaceuticals Inc., and Onyx Pharmaceuticals Inc. v. Mylan Pharmaceuticals Inc. and Mylan Inc.*
Under Seal—Notice of certification letter on behalf of Mylan Pharmaceuticals Inc. ("Mylan") marked "Confidential" to Bayer Healthcare LLC, ("Bayer"), the holder of approved New Drug Application ("NDA") No. 21923 Nexavar® tablets, based on U.S. Pat. No. 7,897,623; 7,235,576; 7,351,834; 8,877,933 and 8,841,330.
Complaint; C.A. No. 15-1162-LPS; filed Dec. 17, 2015; Page ID #1, 29 pages.
Exhibit A; C.A. No. 15-1162-LPS; filed Dec. 17, 2015; Page ID #30, 306 pages.
Civil Cover Sheet; C.A. No. 15-1162-LPS; filed Dec. 17, 2015; Page ID #336, 2 pages.
District of Delaware Local Rule 73.1; C.A. No. 15-1162-LPS; filed Dec. 17, 2015; Page ID #338; 3 pages.

(56) References Cited

OTHER PUBLICATIONS

Supplemental Information for Patent Cases Involving an Abbreviated New Drug Application (ANDA); C.A. No. 115-1162-LPS; filed Dec. 17, 2015; Page ID #341, 1 page.
Report on the Filing or Determination of an Action Regarding a Patent or Trademark; C.A. No. 15-1162-LPS; filed Dec. 17, 2015; Page ID #342; 1 page.
Plaintiffs Bayer Healthcare LLC and Bayer Healthcare Pharmaceuticals Inc.'s Fed. R. Civ. P. 7.1 Statement; C.A. No. 15-1162-LPS; filed Dec. 17, 2015; Page ID #343; 1 page.
Plaintiff Onyx Pharmaceuticals, Inc.'s Fed. R. Civ. P. 7.1 Statement; C.A. No. 15-1162-LPS; filed Dec. 17, 2015; Page ID # 344; 1 page.
Summons in a Civil Action; C.A. 15-1162-LPS; filed Dec. 17, 2015; 2 pages.
Declaration of Mailing; C.A. No. 15-1162-UNA; filed Dec. 21, 2015; Page ID #347 1 page.
Exhibit A; C.A. No. 15-1162-LPS; filed Dec. 21, 2015; Page ID # 348; 6 pages.
Defendants Mylan Pharmaceuticals Inc. and Mylan Inc.'s Motion to Dismiss for Lack of Personal Jurisdiction; C.A. No. 156-1162-LPS; filed Jan. 8, 2016; Page ID #354; 2 pages.
Proposed Order; C.A. No. 15-1162-LPS; filed Jan. 8, 2016; Page ID #356, 1 page.
Defendants Mylan Pharmaceuticals Inc. and Mylan Inc.'s Rule 7.1 Corporate Disclosure Statement; filed Jan. 8, 2016; Page ID #391, 2 pages.
Opening Brief in Support of Mylan Pharmeceuditals Inc. and Mulan Inc.'s Motion to Dismiss for Lack of Personal Jurisdiction and Improper Venue; C.A. No. 15-1162-LPS; filed Jan. 15, 2016; Page ID #393, 27 pages.
Declaration of Frank Mullery in Suport of Mylan Pharmaceuticals Inc. and Mylan Inc.'s Motion to Dismiss for Lack of Personal Jurisdiction and Improper Venue C.A. No. 15-1162-LPS; filed Jan. 15, 2016; Page ID #420; 5 pages.
Stipulation for Extension of Time to Respond to Motion to Dismiss; C.A. No. 15-1162-LPS; filed Jan. 15, 2016; Page ID #425; 1 page.
Motion for Admission Pro Hac Vice; C.A. No. 15-1162-LPS; filed Jan. 20, 2016; Page ID #426, 5 pages.
Stipulation for Extension of Time to Respond to Motion to Dismiss; C.A. No. 15-1162-LPS; filed Jan. 27, 2016; Page ID #431; 1 page.
Stipulation and Proposed Order Dismissing Without Prejudice Defendant Mylan Inc. and Amending Caption to Reflect Same; C.A. No. 15-1162-LPS; filed Feb. 1, 2016; Page ID #432; 5 pages.
Stipulation for Extension of Time; C.A. No. 15-1162-LPS; filed Feb. 23, 2016; Page ID #437; 2 pages.
Defendant Mylan Pharmaceuticals Inc.'s Answer; C.A. No. 15-1162-LPS; filed Feb. 29, 2-016; Page ID #439; 38 pages
Joint Stipulation and Proposed Order to Consolidate; C.A. No. 15-1162-LPS; filed Mar. 8, 2016; Page ID #477; 2 pages.
Memorandum Order; C.A. No. 15-1162-LPS; filed Mar. 30, 2016; Page ID #479, 3 pages.
Summary Translation of Hanmi Rebuttal Brief with Exhibits K7-K12.
Clark et al., Safety and Pharmacokinetics of the Dual Action Raf Kinase and Vascular Endothelial Growth Factor Receptor Inhibitor, BAY 43-9006, in Patients with Advanced, Refractory Solid Tumors; American Association for Cancer Research; 2005; pp. 5472-5480.
Order, Intellectual Property Tribunal 7th Division Decision; Case No. 2015 Dang 865; Invalidation Action Against Patent No. 10-1335932; Petitioner Hanmi Pharm. Co., Ltd.; Respondent Bayer Healthcare LLC, pp. 1-4.
Summary English Translation of Intellectual Property Tribunal 7th Division Decision; Case No. 2015 Dang 865; Invalidation Action Against Patent No. 10-1335932; Petitioner Hanmi Pharm. Co., Ltd.; Respondent Bayer Healthcare LLC; pp. 1-19.
Breccia et al., "Imatinib Treatment in Chronic Myelogenous Leukemia: What Have We Learned So Far?", Cancer letters 300 (2011) pp. 115-121.
Osterberg et al., "Adherence to Medication"; The New England Journal of Medicine; 2005; 353: pp. 487-497.
Strumberg et al., "Phase I Clinical and Pharmacokinetic Study of the Novel Raf Kinase and Vascular Endothelial Growth Factor Receptor Inhibitor BAY 43-9006 in Patients With Advanced Refractory Solid Tumors", Journal of Clinical Oncology; vol. 23, No. 5, Feb. 10, 2005; pp. 965-972.
Summary English Translation of Petition for Patent Invalidation; Case No. 2015 Dang 1545 Patent Invalidation Action; Petitioner JW Pharmaceutical Co., Ltd. Respondent Bayer Healthcare LLC, Korean Patent No. 10-1335932; pp. 1-3.
Summary English Translation of Petition for Patent Invalidation; Case No. 2015 Dang 1602 Patent Invalidation Action; Petitioner Ahngook Pharmaceutical Co., Ltd.; Respondent Bayer Healthcare LLC; Korean Patent No. 10-1335932, pp. 1-2.
Summary English Translation of Petition for Patent Invalidation; Case No. 2015 Dang 1511 Patent Invalidation Action; Petitioner Yuhan Corp. Respondent Bayer Healthcare LLC; Korean Patent No. 10-1335932; pp. 1-4.
Summary English Translation of Petition for Patent Invalidation; Case No. 2015 Dang 865 Patent Invalidation Action; Petitioner Hanmi Pharm. Co., Ltd.; Respondent Bayer Healthcare LLC, Korean Patent No. 10-1335932; pp. 1-10.
Summary English Translation of Comprehensive Brief; Case No. 2015 Dang 865 Patent Invalidation Action; Petitioner Hanmi Pharm. Co., Ltd.; Respondent Bayer Healthcare LLC; pp. 1-3.
Summary English Translation of Petition for Patent Invalidation; Case No. 2015 Dang 1602 Patent Invalidation Action; Petitioner Ahngook Pharmaceutical Co., Ltd.; Respondent Bayer Healthcare LLC; Korean patent No. 10-1335932; pp. 1-2.
Rasenack et al., "Microcyrstals for Dissolution Rate Enhancement of Poorly Water-soluble Drugs"; International Journal of Pharmaceutics; 254 (2003 pp. 137-145.
Complaint; C.A. No. 15-114-LPS; filed Jan. 30, 2015, 15 pages.
Exhibit A, U.S. Pat. No. 8,618,141 and U.S. Pat. No. 8,877,933; C.A. No. 15-114-LPS; filed Jan. 30, 2015, 61 pages.
Civil Cover Sheet; C.A. No. 15-114-LPS; filed Jan. 30, 2015, 2 pages.
District of Delaware Local Rule 73.1; C.A. No. 15-114-LPS; filed Jan. 30, 2015; 3 pages.
Supplemental Information for Patent Cases Involving an Abbreviated New Drug Application (ANDA); C.A. No. 15-114-LPS; filed Jan. 30, 2015; 1 page.
Report on The Filing or Determination of an Action Regarding a Patent or Trademark; C.A. No. 14-115-LPS, filed Jan. 30, 2015, 1 page.
Plaintiffs Bayer Healthcare LLC and Bayer Healthcare Pharmaceuticals Inc.'s Fed. R. Civ. P. 7.1 Statement; C.A. No. 15-114-LPS; filed Jan. 30, 2015; 1 page.
Plaintiff Oxyx Pharmaceuticals, Inc.'s Fed. R. Civ. P. 7.1 Statement; C.A. No. 15-114-LPS; filed Jan. 30, 2015, 1 page.
Summons in a Civil Action; C.A. No. 15-114-LPS; filed Jan. 30, 2015; 2 pages.
Declaration of Mailing; C.A. No. 15-114-LPS filed Jan. 30, 2015; 9 pages.
Stipulation for Extension of Time; C.A. No. 15-114-LPS; filed Jan. 30, 2015; 2 pages.
Entry of Appearance; C.A. No. 15-114-LPS; filed Jan. 30, 2015; 1 page.
Stipulation for Extension of Time; C.A. No. 15-114-LPS; filed Jan. 30, 2015, 2 pages.
Defendants Mylan Pharmaceuticals Inc. and Mylan Inc.'s Motion to Dismiss for Lack of Personal Jurisdiction; C.A. No. 15-114-LPS; filed Apr. 24, 2015, 1 page.
Proposed Order; C.A. No. 15-114-LPS; filed Apr. 24, 2015, 1 page.
Defendants Mylan Pharmaceuticals Inc. and Mylan Inc.'s Rule 7.1 Corporate Disclosure Statement; C.A. No. 15-115-LPS; filed Apr. 24, 2015; 2 pages.
Motion and Order for Admission Pro Hac Vice; C.A. No. 15-114-LPS; filed Apr. 29, 2015, 9 pages.
Brief in Support of Mylan Pharmaceuticals Inc. and Mylan Inc.'s Motion to Dismiss for Lack of Personal Jurisdiction; C.A. No. 15-114-LPS; filed May 4, 2015; 26 pages.

(56) References Cited

OTHER PUBLICATIONS

Declaration of Frank Mullery in Support of Mylan Pharmaceuticals Inc. and Mylan Inc.'s Motion to Dismiss for Lack of Personal Jurisdiction; C.A. No. 15-114-LPS; filed May 4, 2015; 5 pages.
Joint Stipulation to Extend Time for Plaintiffs to Respond to Defendants' Motion to Dismiss; C.A. No. 15-114-LPS; filed May 5, 2015, 2 pages.
Motion for Admission Pro Hac Vice; C.A. No. 15-114-LPS; filed May 13, 2015, 5 pages.
Stipulation for Extension of Time; C.A. No. 15-114-LPS; filed May 29, 2015, 2 pages.
Plaintiffs' Answering Brief in Opposition to Defendants' Motion to Dismiss for Lack of Personal Jurisdiction; C.A. No. 15-114-LPS; filed Jun. 3, 2015; 26 pages.
Exhibit A, C.A. No. 15-114-LPS; filed Jun. 3, 2015, 41 pages.
Reply in Support of Mylan Pharmaceuticals Inc. and Mylan Inc.'s Motion to Dismiss for Lack of Personal Jurisdiction; C.A. No. 15-114-LPS, 15 pages.
Exhibit A, C.A. No. 15-114-LPS; filed Jun. 22, 2015, 15 pages.
Notice of Withdrawal; C.A. No. 15-114-LPS; filed Jul. 9, 2015; 1 page.
Notice of Withdrawal of Counsel; C.A. 15-114-LPS; filed Aug. 7, 2015, 2 pages.
Motion for Admission Pro Hac Vice; C.A. No. 15-114-LPS; filed Aug. 21, 2015, 3 pages.
Stipulation for Extension of Time; C.A. No. 15-114-LPS; filed Aug. 26, 2015; 2 pages.
Stipulation for Extension of Time; C.A. No. 15-114-LPS; filed Sep. 14, 2015; 2 pages.
Proposed Scheduling Order; C.A. No. 15-114-LPS; filed Sep. 22, 2015; 12 pages.
Motion and Order for Admission Pro Hac Vice; C.A. No. 15-114-LPS; filed Sep. 29, 2015; 5 pages.
Scheduling Order; C.A. No. 15-114-LPS; filed Oct. 14, 2015; 12 pages.
Stipulation for Extension of Time; C.A. No. 15-114-LPS; filed Oct. 23, 2015; 2 pages.
Notice of Service; C.A. No. 15-114-LPS; filed Oct. 26, 2015, Page ID #428; 2 pages.
Notice of Service; C.A. No. 15-114-LPS; filed Oct. 26, 2015, Page ID #430; 2 pages.
Notice of Service; C.A. No. 15-114-LPS; filed Oct. 26, 2015, Page ID #432; 2 pages.
Order Scheduling ADR Teleconference; C.A. No. 15-114-LPS; filed Oct. 22, 2015, Page ID #434, 4 pages.
Stipulation for Extension of Time; C.A. No. 15-114-LPS; filed Nov. 4, 2015; Page ID #438, 2 pages.
Stipulation for Extension of time; C.A. No. 15-114-LPS; filed Nov. 10, 2015; Page ID #440; 2 pages.
Motion for Admission Pro Hac Vice; C.A. No. 15-114-LPS; filed Nov. 16, 2015; Page ID #442; 3 pages.
Stipulated Protective Order; C.A. No. 15-114-LPS; filed Nov. 24, 2015; Page ID #445; 30 pages.
Notice of Service; C.A. No. 15-114-LPS; filed Dec. 3, 2015; Page ID #475; 2 pages.
Notice of Service; C.A. No. 15-114-LPS; field Jan. 21, 2016; Page ID #477; 4 pages.
Notice of Service; C.A. No. 15-114-LPS; filed Jan. 21, 2016; Page ID #481; 4 pages.
Stipulation and Proposed Order Dismissing Without Prejudice Defendant Mylan Inc. and Amending Caption to Reflect Same; C.A. No. 15-114-LPS; filed Feb. 1, 2016; Page ID #485; 5 pages.
Stipulation for Extension of Time; C.A. No. 15-114-LPS; filed Feb. 24, 2016; Page ID #490; 2 pages.
Notice of Service; C.A. No. 15-114-LPS; fled Feb. 25, 2016; 2 pages.
Defendant Mylan Pharmaceuticals Inc.'s Answer; C.A. No. 15-114-LPS; filed Feb. 29, 2016; Page ID #494, 20 pages.
Joint Stipulation and Proposed Order to Consolidate; C.A. No. 15-114-LPS; filed Mar. 8, 2016; Page ID #514, 2 pages.
Joint Stipulation to Extend Time; C.A. No. 15-114-LPS; filed Mar. 21, 2016; Page ID #516, 2 pages.
Letter to The Honorable Leonard P. Stark dated Mar. 28, 2016; C.A. No. 15-114-LPS; filed Mar. 28, 2016; Page ID #518; 2 pages.
Exhibit 1; C.A. No. 15-114-LPS; filed Mar. 28, 2016, Page ID #520, 4 pages.
Letter to the Honorable Leonard P. Stark dated Mar. 28, 2016; C.A. No. 15-114-LPS; filed Mar. 28, 2016; Page ID #524, 5 pages.
Notice of Service; C.A. No. 15-114-LPS; filed Mar. 28, 2016; Page ID #529; 2 pages.
Notice of Service; C.A. No. 15-114-LPS; filed Mar. 29, 2016; Page ID #531; 2 pages.
Letter to the Honorable Leonard P. Stark dated Mar. 29, 2016; C.A. No. 15-114-LPS; filed Mar. 29, 2016, Page ID #533, 2 pages.
Letter to the honorable Leonard P. Stark dated Mar. 29, 2016; C.A. No. 15-114-LPS; filed Mar. 29, 2016; Page ID #535, 2 pages.
Memorandum Order; C.A. No. 15-114-LPS; filed 30, 2016; Page ID #537, 3 pages.
Notice of Service; C.A. No. 15-114-LPS; filed Mar. 30, 2016; Page ID #540, 2 pages.
Motion and Order for Admission Pro Hac Vice; filed Apr. 27, 2016; Page ID #542; 5 pages.
Notice of With Withdrawal of Certain Pro Hac Vice Counsel; filed May 5, 2016; Page ID #547; 2 pages.
Notice of Service; C.A. No. 15-114-LPS; filed May 31, 2016; 2 pages.
Notice of Service; C.A. No. 15-114-LPS; filed May 6, 2016; 2 pages.
Onyx Pharmaceuticals, Inc.'s First Supplemental Responses to Defendants' First Set of Requests for Production of Documents and Things Nos. 1-118; C.A. No. 15-114-LPS; filed May 31, 2016, 8 pages.
Bayer Healthcare LLC and Bayer Healthcare Pharmaceutical Inc.'s Initial Disclosures; C.A. No. 115-114-LPS; filed Oct. 26, 2015; 4 pages.
Onyx Pharmaceuticals, Inc.'s Initial Disclosures Pursuant to Rule 26(a)(1); C.A. No. 15-114-LPS; filed Oct. 26, 2015; 4 pages.
Plaintiffs Bayer Healthcare LLC and Bayer Healthcare Pharmaceuticals Inc. Responses and Objections to Defendants' First Set of Requests fro Production (Nos. 1-118); C.A. 15-114-LPS; filed Jan. 21, 2016; 93 pages.
Onyx Pharmaceuticals, Inc.'s Responses to Defendants' First Set of Requests for Production of Documents and Things (Nos. 1-118); C.A. No. 15-114-LPS; filed Jan. 21, 2016; 99 pages.
Plaintiffs' First Set of Interrogatories to Defendants Mylan Pharmaceuticals Inc. and Mylan Inc.; C.A. No. 15-114-LPS; filed Jan. 21, 2016, 6 pages.
Plaintiffs' Initial Identification of Asserted Patents and Accused Products; C.A. No. 15-114-LPS; filed Mar. 28, 2016, 2 pages.
Bayer Heathcare LLC and Bayer Healthcare Pharmaceutical Inc.'s Supplemental Initial Disclosures; C.A. No. 15-114-LPS; filed Mar. 29, 2015; 5 pages.
Onxy Pharmaceuticals, Inc.'s Supplemental Initial Disclosures Pursuant to Rule 26(a)(1); C.A. No. 15-114-LPS; filed Mar. 30, 2015, 4 pages.
Stipulation for Extension of Time to Respond to Motion to Dismiss; C.A. No, 15-1162-LPS; filed Jan. 27, 2016; Page ID #431; 1 page.
Defendant Mylan Pharmaceuticals Inc.'s Answer; C.A. No. 15-1162-LPS; filed Feb. 29, 2-016; Page ID #439; 38 pages.
Ahmad et al., "Kinase Inhibition with BAY 43-9006 in Renal Cell Carcinoma"; Clinical Cancer Research; vol. 10, 6388s-6392s, Sep. 15, 2004 (Suppl.).
Drugs of the Future 2002, 27(12): 11-41-147; "Oncolytic Raf Kinase Inhibitor"; BAY 43-9006; pp. 1-7.
Korean Patent Court Opponents Appeal Brief; Case No. 2016 Heo 4733 Patent Invalidation; Appellant: Hanmi Pharmaceutical Co., Ltd.; Appellee: Bayer HealthCare LLC, pp. 1-28 and Summary translation pp. 1-7.
Pharmaceutics: The Science of Dosage Form Design; Edited by Michael E. Aulton; Churchill Livingstone Edinburgh London Melbourne and New York 1988.
Opponents Reply in Opposition Against EP 1868579; dated Apr. 14, 2016; pp. 1-25.

(56) References Cited

OTHER PUBLICATIONS

Opponents Reply in Opposition Against EP 1868579; dated Sep. 3, 2014, pp. 1-25.
EP Opponents Affidavit of Dr. Schubert-Zsilavecz, discussed in item 6, (EP Opponents Reply in Opposition Against EP 1868579, dated Sep. 3, 2014 pp. 1-25).
Pharmaceutical Dosage Forms: Tablets, vol. 1, Marcel Dekker, Inc., 1989.
Guidance for Industry, U.S. Department of Health and Human Services, Food and Drug Administration, Jan. 1999.
Korean Patent Court Opponents Rebuttal Brief; Case No. 2016 Heo 4733 Patent Invalidation; Appellant: Hanmi Pharmaceutical Co., Ltd.; Appellee: Bayer HealthCare LLC, pp. 1-28 and Summary translation pp. 1-8.
DE-1 Complaint filed by Bayer HealthCare LLC, et al.
DE-1-1 Exhibits A-D to the Complaint filed by Bayer HealthCare LLC, et al.
DE-3 Report of filing by Bayer HeathCare LLC to USPTO.
DE-4 Supplemental information provided by Bayer HealthCare LLC, et al., regarding ANDA.
DE-5 Plaintiff's Statement under Rule 7.1(a).
DE-10 Answer filed by Teva Pharmaceuticals USA, Inc.
DE-11 Defendant Statement under Rule 7.1(a).
DE-13 Bayer HealthCare LLC, et al.'s Answer to counter claims.
A-1 Four Versions of Second Amended Answer & Counterclaims.
B-1 Defendant's Fourth Supplemental Objections and Responses to Plaintiffs First Set of Interrogatories, pp. 1-140.
C-1 Plaintiffs Second Supplemental Response and Objections to Defendant's Interrogatory No. 6, pp. 1-54.
D-1 Allegedly Showing Public Use Bayer Nexavar.
E-1 Statements of Investigator.
E-2 Patient Information & Consent forms.
E-3 Documents in Response to Execution Page.
E-4 Letter to Ramon Vargas, MD, dated Aug. 23, 2002 1 page, Informed Consent, Protocol # 100483, Sponsor Bayer Corporation, Investigator, Ramon Vargas, MD, pp. 1-6.
E-5 Protocols.
F-1 Raf Kinase Inhibitor (BAY 43-9006 / BAY 54-9085): Development of a Solid Dosage Form (Tablet) for Phase I, Report No. MRC-01045, Jun. 26, 2000, pp. 1-92.
G-1 Expert Report of Dr. Jerry L. Atwood, Ph.D., pp. 1-12.
G-2 Opening Expert Report of Mark D. Hollingsworth, Ph.D., pp. 1-130.
H-1 Dumas et al., "Raf Kinase Inhibitors for the Treatment of Cancer: Diphenyl Urea Series (BAY 43-9006)," May 6, 2000, Bayer Nexavar, pp. 02951029-02952325.
H-2 BAY 54-9085, Analytical Status of Drug Substance International Technical Conference 2001, Leverkusen, Germany, Bayer Nexavar, pp. 02952318-02952326.
Israel Opposition, Statement of Case on Behalf of the Opponent, Patent Registration Application No. 185517, Teva Pharmaceutical Industries Ltd., pp. 1-38.
English language translation of Israel Opposition, Statement of Case on Behalf of the Opponent, Patent Registration Application No. 185517, Teva Pharmaceutical Industries Ltd., pp. 1-38.
Michael E. Aulton, Ed. Pharmaceutics: The Science of Dosage Form Design, Churchill Livingstone, Edinburgh London Melbourne and New York 1988, pp. 304-314 and 647-655.
Alfonso R. Gennaro, Ed. 20th Edition "Remington: The Science and Practice of Pharmacy", Oral Solid Dosage Forms, Edward M. Rudnic, PHD., Chapter 45, (2000), pp. 858-870.
Walter Lund, Ed. "The Pharmaceutical Codex", Twelfth Edition, Principles and Practice of Pharmaceutics, London The Pharmaceutical Press 1994, pp. 2-11 and 198-201.
Lowinger et al., "Design and Discovery of Small Molecules Targeting Raf-1 Kinase", Current Pharmaceutical Design, . 2002, Betham Science Publishers Ltd., 2002, 8, pp. 2269-2278.
Hotte, et al., "BAY 43-9006: Early Clinical Data in Patients with Advanced Solid Malignancies", Current Pharmaceutical Design, 2002, Betham Science Publishers Ltd., 2002, pp. 2249-2253.

Strumberg et al., "Phase I Clinical and Pharmacokinetic Study of the Novel Raf Kinase and Vascular Endothelial Growth Factor Receptor Inhibitor BAY 43-9006 in Patients With Advanced Refractory Solid Tumors," vol. 23, No. 5, Feb. 10, 2005, Journal of Clinical Oncology, Original Report, pp. 965-972.
Kathleen M. Lee, "Overview of Drug Product Development," Current Protocols in Pharmacology, 2001 John Wiley & Sons, Inc., pp. 7.3.1-7.3.10.
Rasenack et al., "Microcyrstals for Dissolution Rate Enhancement of Poorly Water-Soluble Drugs", International Journal of Pharmaceutics 254(2003), pp. 137-145.
Lachman et al., "The Theory and Practice of Industrial Pharmacy", Third Edition, Lea & Febiger, 1986, Philadelphia, pp. 296-302 and 325-327.
Ahmad et al., Kinase Inhibition with BAY 43-9006 in Renal Cell Carcinoma:, vol. 10 Sep. 15, 2004, pp. 6388s-6392s.
Israel National Phase of International Patent Application National Phase, PCT/EP05/10119, Thermodynamically stable form of BAY 43-9006 tosylate, Sep. 20, 2005, pp. 1-37.
Israel National Phase of International Patent Application No. 144030, PCT/US/2000/000648, Omega-Carboxlyaryl Substituted Diphenyl Ureas, Pharmaceutical Compositions Comprising Them and Their Use for The Preparation of Medicaments for Inhibiting Raf Kinase, Jun. 27, 2001, pp. 1-103.
Lieberman et al., "Pharmaceutical Dosage Forms: Tablets vol. 1, Second Edition, Revised and Expanded", J-1, pp. 80-120.
Lieberman et al., "Pharmaceutical Dosage Forms: Tablets vol. 1, Second Edition, Revised and Expanded", J-2, pp. 131-179.
114—Motion by Mylan to Amend Pleading, Apr. 19, 2017.
115—Letter to Judge Stark from Mylan to Amend Answer to Please Inequitable conduct, Apr. 19, 2017.
121—Letter to Judge Stark from Bayer Apr. 27, 2017.
127—Letter to Judge Stark, Apr. 19, 2017.
128—Letter to Judge Stark from Bayer May 10, 2017.
128-1—Exhibits A-D to Letter to Judge Stark from Bayer May 10, 2017.
129—Letter to Judge Stark from Mylan May 15, 2017.
150—Expert Report of Michael Grossbard, M.D., pp. 1-88.
151—Expert Report of Dr. Ron Bihousky, pp. 1-88.
160—European Opposition for EP Patent 1,797,038.
Syed et al.,"Novel Therapies for Renal Cell Carcinoma", Division of Medical Oncology, University of Texas Health Science Center at San Antonio, 16 pages.
Riedl, et al., #4956 "Potent Raf Kinase Inhibitors from the Diphenylurea Class: Structure Activity Relationships," Proceedings of the American Association for Cancer research, vol. 42, Mar. 2001 (Mar. 2001), p. 923,92nd Annual Meeting of the American Association for Cancer Research; New Orleans, LA, USA; Mar. 24-28, 2001.
Lowinger, "Design and Discovery of Small Molecules Targeting Raf-1 Kinase," Current Pharmaceutical Design, 2002, vol. 8, pp. 2269-2278.
Wilhelm et al,. "Discovery and Development of Sorafenib: A Multikinase Inhibitor for Treating Cancer", Nature Reviews, Drug Discovery, vol. 5, Oct. 2006, pp. 835-844.
Kolch et al., "Raf-1 Protein Kinase is Required for Growth of Induced NIH/3T3 Cells", Letters of Nature, Nature, vol. 349, Jan. 31, 1991, pp. 426-428.
Simone, Joseph, V., "Part XIV. Oncology," in: Cecil Textbook of Medicine, 20th Edition, vol. 1, Feb. 3, 1997. W.B. Saunders Company, pp. 1004-1010.
Johnson, et al., Relationships Between Drug Activity in NCI Preclinical in Vitro and In Vivo Model.
Pearce, et al. "Failure modes in anticancer drug discovery and development," Chapter 18, Cancer Drug Design and Discovery, pp. 424-434.
Gura; Cancer Models: Systems for Identifying New Drugs Are Often Faulty, Science, Nov. 7, 1997, pp. 30086830-0086835.
Monia, et al., "Antitumor activity of a phosphorothioate antisense oligodeoxynucleotide targeted against C-raf Kinase," Nature Medicine, vol. 2, No. 6, Jun. 1996, pp. 668-675.

(56) References Cited

OTHER PUBLICATIONS

Smith, et al., "Recent Advances in the Research and Development of RAF Kinase Inhibitors," Current Topics in Medicinal Chemistry, 2006, 6, pp. 1071-1089.
Dumas, J. "Protein kinase inhibitors from the urea class," Curr. Opin. in Drug Discovery adn Dev., 5(s):718-727, 2002.
Bruix, et al., "Management of Hepatocellular Carcinoma", AASLD Practice Guideline, pp. 1208-1236.
Sobara et al., "BAY-43-9006," Drugs of the Future, 2002, vol. 27, No. 12, pp. 1141-1147.

* cited by examiner

PHARMACEUTICAL COMPOSITION FOR THE TREATMENT OF CANCER

RELATED APPLICATIONS/PATENTS

This application is a National Stage Application filed under 35 U.S.C. §371 based on International Application No. PCT/EP2006/001574, filed Feb. 22, 2006, which claims priority to U.S. Provisional Application Ser. No. 60/658,827, filed Mar. 7, 2005, the entire contents each of which are incorporated herein by reference.

FIELD OF THE INVENTION

This invention relates to novel pharmaceutical compositions and their use for treating hyper-proliferative disorders such as cancer, either as a sole agent or in combination with other anti-cancer therapies and their process for preparing.

BACKGROUND OF THE INVENTION

Diarylureas are a class of serine-threonine kinase inhibitors as well as tyrosine kinase inhibitors known in the art (Smith et al., *Bioorg. Med. Chem. Lett.* 2001, 11, 2775-2778, Lowinger et al., *Clin. Cancer Res.* 2000, 6(suppl.), 335, Lyons et al., *Endocr.-Relat. Cancer* 2001, 8, 219-225, Lowinger et al., *Curr. Pharm. Design* 2002, 8, 99-110). Omega-Carboxyaryl diphenyl ureas are disclosed in WO00/42012 and WO00/41698. In particular, it has been discovered that the diphenyl urea of formula (I),

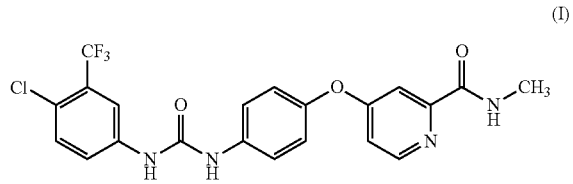 [SMILES: CNC(=O)c1cc(Oc2ccc(NC(=O)Nc3ccc(Cl)c(C(F)(F)F)c3)cc2)ccn1]

(I)

also referred as "BAY 43-9006" or 4-{4-[({[4-chloro-3-(trifluoromethyl)phenyl]amino}carbonyl)-amino]phenoxy}-N-methylpyridine-2-carboxamide, and its pharmaceutically acceptable salts are potent inhibitors of raf, VEGFR-2, p38, and PDGFR kinases. These enzymes are all molecular targets of interest for the treatment of hyper-proliferative diseases, including cancer. Therefore, the compound of formula (I) will be used as medicine for the treatment of the above mentioned diseases.

Despite the progress described in the art with regard to kinase inhibitors, there remains a need for improved medicines for the treatment of cancer. In particular, there remains a need for improved oral pharmaceutical compositions which can be taken in easily and therefore would increase the patient's compliance. The oral pharmaceutical composition has to provide a plasma level of the active agent which is sufficient for an effective therapy. This is dependent on the solubility and the release behavior of the active agent. In the case of a solid pharmaceutical composition the dissolution properties and chemical and mechanical stability are of importance. In order to support a high compliance the oral pharmaceutical composition should not have to be taken in more than three times a day, the less the better, and in the case of a tablet the dimensions of the tablet should not be too large to allow a good swallowing. The dimensions of a tablet are dependent on the amount of the active agent needed for an effective therapy and the amounts of the excipients. Type and amount of the excipients in combination with the process for preparing are essential for release properties, bioavailability of the compound in mammals, stability and the industrial applicability of the manufacturing process of the pharmaceutical composition.

The objective of the present invention is to provide a pharmaceutical composition comprising the compound of formula (I) which should be applied no more then three times a day in order to achieve an effective plasma level of the compound of formula (I). In the case of a tablet or capsule as oral pharmaceutical composition it should not be too large to provide good swallowing and no more than two should have to be taken in at the same time.

DESCRIPTION OF THE INVENTION

The present invention pertains to a pharmaceutical composition comprising the compound of the formula (I) in a high concentration and at least one pharmaceutically acceptable excipient, the use of the composition for the treatment of hyper-proliferative diseases, such as cancer, either as a sole agent, or in combination with other anti-cancer therapies, and the process for preparing of said composition.

Surprisingly the pharmaceutical composition according to the invention has a good bioavailability of the compound of the formula (I), and an effective plasma level is achieved. Furthermore the pharmaceutical composition according to the invention provides a good stability of the compound of the formula (I).

Although the tablets according to the invention are high concentrated on the compound of the formula (I), they surprisingly show good release properties, good bioavailability, high stability and a sufficient hardness. Due to the fact that the pharmaceutical composition according to the invention comprises the compound of the formula (I) in a high concentration dimensions of the composition can be realized which allow a good swallowing of the composition. Therefore the pharmaceutical composition can be taken in easily and supports a high compliance.

The term "the compound of formula (I)", "active agent" or "the compound of this invention" does not only refer to 4{4-[3-(4-chloro-3-trifluoromethylphenyl)-ureido]-phenoxy}-pyridine-2-carboxylic acid methyl amide as depicted in Formula I, but also refers to its polymorphs, solvates, hydrates, pharmaceutically acceptable salts, or a combination thereof.

Suitable pharmaceutically acceptable salts are well known to those skilled in the art and include salts of inorganic and organic acids, such as hydrochloric acid, hydrobromic acid, sulfuric acid, phosphoric acid, methanesulphonic acid, trifluoromethanesulfonic acid, benzenesulfonic acid, p-toluenesulfonic acid (tosylate salt), 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4- diazabiclo[2.2.2]octane (DABCO), 1,5-diazabicyclo[4.3.0]-non-5-ene (DBN) and 1,8-diazabicyclo[5.4.0]undec-7-ene (DBU).

Solvates for the purposes of the invention are those forms of the compounds where solvent molecules form a complex in the solid state and include, but are not limited to for example ethanol and methanol. Hydrates are a specific form of solvates, where the solvent molecule is water.

Preferably used in the pharmaceutical composition according to the invention is the p-toluene-sulfonic acid salt of 4{4-[3-(4-chloro-3-trifluoromethylphenyl)-ureido]-phenoxy}-pyridine-2-carboxylic acid methyl amide (tosylate salt of compound (I)). More preferably the p-toluene-sulfonic acid salt of 4{4-[3-(4-chloro-3-trifluoromethylphenyl)-ureido]-phenoxy}-pyridine-2-carboxylic acid methyl amide exists for at least 80% in the stable polymorph I. Most preferably the p-toluenesulfonic acid salt of 4{4-[3-(4-chloro-3-trifluoromethylphenyl)-ureido]-phenoxy}-pyridine-2-carboxylic acid methyl amide exists for at least 80% in the stable polymorph I and in a micronized form.

Micronization can be achieved by standard milling methods, preferably by air chat milling, known to a skilled person. The micronized form can have a mean particle size of from 0.5 to 10 µm, preferably from 1 to 6 µm, more preferably from 1 to 3 µm. The indicated particle size is the mean of the particle size distribution measured by laser diffraction known to a skilled person (measuring device: HELOS, Sympatec).

The process for preparing the p-toluenesulfonic acid salt of 4{4-[3-(4-chloro-3-trifluoromethyl-phenyl)-ureido]-phenoxy}-pyridine-2-carboxylic acid methyl amide and its stable polymorph I are described in the patent applications EP 04023131.8 and EP 04023130.0.

The inventive pharmaceutical composition comprises the compound of formula (I) in a portion of at least 40%, preferably at least 45%, more preferably at least 50, most preferably at least 55% by weight of the composition.

Preference is given to a pharmaceutical composition comprising the p-toluenesulfonic acid salt of 4{4-[3-(4-chloro-3-trifluoromethylphenyl)-ureido]-phenoxy}-pyridine-2-carboxylic acid methyl amide in a portion of at least 55%, preferably at least 62%, more preferably at least 69%, most preferably at least 75% by weight of the composition.

The total amount of the active ingredient (compound of Formula I) to be administered preferably via the oral route using the pharmaceutical composition of the present invention will generally range from about 0.1 mg/kg to about 50 mg/kg body weight per day. Based upon standard laboratory techniques known to evaluate compounds useful for the treatment of hyper-proliferative disorders, by standard toxicity tests and by standard pharmacological assays for the determination of treatment of the conditions identified above in mammals, and by comparison of these results with the results of known medicaments that are used to treat these conditions, the effective dosage of the pharmaceutical compositions of this invention can readily be determined by those skilled in the art. The amount of the administered active ingredient can vary widely according to such considerations as the particular compound and dosage unit employed, the mode and time of administration, the period of treatment, the age, sex, and general condition of the patient treated, the nature and extent of the condition treated, the rate of drug metabolism and excretion, the potential drug combinations and drug-drug interactions, and the like.

Preference is given to an amount of the compound of formula (I) in the pharmaceutical composition from 20 to 2000 mg, preferably from 40 to 800 mg, more preferably from 50 to 600 mg.

Particular preference is given to an amount of p-toluenesulfonic acid salt of 4{(4-[3-(4-chloro-3-trifluoromethylphenyl)-ureido]-phenoxy}-pyridine-2-carboxylic acid methyl amide in the pharmaceutical composition from 27 to 2740 mg, preferably from 54 to 1096, more preferably from 68 to 822 mg.

The pharmaceutical composition according to the invention is administered one or more, preferably up to three, more preferably up to two times per day. Preference is given to an administration via the oral route. With each administration the number of tablets or capsules taken in at the same time should not exceed two.

Nevertheless, it may in some cases be advantageous to deviate from the amounts specified, depending on body weight, individual behavior toward the active ingredient, type of preparation and time or interval over which the administration is effected. For instance, less than the aforementioned minimum amounts may be sufficient in some cases, while the upper limit specified has to be exceeded in other cases. In the case of administration of relatively large amounts, it may be advisable to divide these into several individual doses over the day.

This pharmaceutical composition will be utilized to achieve the desired pharmacological effect by pereferably oral administration to a patient in need thereof, and will have advantageous properties in terms of drug release, bioavailability, and/or compliance in mammals. A patient, for the purpose of this invention, is a mammal, including a human, in need of treatment for the particular condition or disease.

The pharmaceutical composition comprises suitable administration forms which deliver the compound of the invention in a rapid manner, for example tablets (uncoated or coated tablets), tablets which disintegrate rapidly in the oral cavity or capsules optionally filled with granules (for example hard or soft gelatin capsules), sugar-coated tablets, powders, sachets, granules, pellets, dragées, chewable tablets, dispersible tables, troches and lozenges.

Preference is given to tablets, granules, capsules optionally filled with granules, pellets, dragées, chewable tablets, dispersible tables, troches and lozenges. More preferably the application forms are tablets, granules and capsules optionally filled with granules. Most preferably the application form is a tablet.

The tablet according to the invention shows for example a hardness of more than 80 N, preferably more than or equal to 100 N.

The pharmaceutical composition according to the invention preferably a tablet or a capsule has dimensions which allows good swallowing. Good swallowing depends also on the used format. The longest dimension for example of an oval tablet or capsule is less than or equal to 25 mm. For example a round tablet should have a diameter less than or equal to 13 mm.

The pharmaceutical composition according to the invention shows good release properties. Furthermore preference is given to administration forms wherein the compound of the invention is delivered in a rapid manner also known as "immediate release" administration form. According to the present invention immediate release administration forms having a Q-value (30 minutes) of 75% due to USP-release method with device 2 (paddle, 75 rpm, in 0.1M HCl+1% sodium dodecylsulfate).

The pharmaceutical composition according to the invention is stable for more than 18 months.

A pharmaceutically acceptable excipient is any excipient which is relatively non-toxic and innocuous to a patient at concentrations consistent with effective activity of the active ingredient so that any side effects ascribable to the excipient do not vitiate the beneficial effects of the active ingredient.

Pharmaceutically acceptable excipients according to the invention are for example disintegrants, binders, lubricants, fillers, plasticizers, surfactants and wetting agents, film-forming agents and coating materials, and coloring agents for example pigments.

Disintegrants include, but are not limited to croscarmellose sodium, crospovidone, alginic acid, carboxymethylcellulose calcium, carboxymethylcellulose sodium, microcrystalline cellulose, hydroxypropyl cellulose, low substituted hydroxypropyl cellulose, polacrillin potassium, cross-linked polyvinylpyrrolidone, sodium alginate, sodium starch glycollate, partially hydrolysed starch, sodium carboxymethyl starch and starch. Preference is given to croscarmellose sodium and/or cross-linked polyvinylpyrrolidone, more preference is given to croscarmellose sodium.

The amount of the disintegrant contained in the pharmaceutical composition of can be from 0 to 15%, preferably from 5 to 12% by the total weight of the composition.

Binders include, but are not limited to hydroxypropyl cellulose, hypromellose (hydroxypropyl methylcellulose, HPMC), microcrystalline cellulose, acacia, alginic acid, carboxymethylcellulose, ethylcellulose, methylcellulose, hydroxaethylcellulose, ethylhydroxyethylcellulose, polyvinyl alcohol, polyacrylates, carboxymethylcellulose calcium, carboxymethylcellulose sodium, compressible sugar, ethylcellulose, gelatin, liquid glucose, methylcellulose, polyvinyl pyrrolidone and pregelatinized starch. Preference is given to a hydrophilic binder which are soluble in the granulation liquid, more preference is given to hypromellose (hydroxypropyl methylcellulose, HPMC) and/or polyvinylpyrrolidone, most preference is given to hypromellose.

The amount of the binder contained in the pharmaceutical composition of can be from 0 to 15%, preferably from 0.5 to 8% by the total weight of the composition.

Lubricants include, but are not limited to calcium stearate, magnesium stearate, mineral oil, stearic acid, fumaric acid, sodium stearylfumarate, zinc stearate and polyethyleneglycol. Preference is given to magnesium stearate.

The amount of the lubricant contained in the pharmaceutical composition of can be from 0 to 2%, preferably from 0.2 to 0.8% by the total weight of the composition.

Fillers include, but are not limited to dibasic calcium phosphate, kaolin, lactose, mannitol, micro-crystalline cellulose, silicated microcrystalline cellulose, dicalcium phosphate, tricalcium phosphate, magnesium trisilicate, mannitol, maltitol, sorbitol, xylitol, lactose for example the anhydrous form or the hydrate form such as the monohydrate form, dextrose, maltose, saccharose, glucose, fructose or maltodextrine, powdered cellulose, precipitated calcium carbonate, sodium carbonate, sodium phosphate and starch. Preference is given to microcrystalline cellulose, mannitol, lactose and/or dicalcium phosphate, more preference is given to microcrystalline cellulose.

The amount of the filler contained in the pharmaceutical composition of can be from 0 to 60%, preferably from 3 to 20 % by the total weight of the composition.

Surfactants and Wetting agents include, but are not limited to heptadecaethylene oxycetanol, lecithins, sorbitol monooleate, polyoxyethylene sorbitol monooleate, polyoxyethylene stearate, polyoxyethylen sorbitan monolaurate, benzalkonium chloride, nonoxynol 10, oxtoxynol 9, polysorbates for example 20, 40, 60 or 80, sorbitan monopalmitate, sodium salts of fatty alcohol-sulfates such as sodium lauryl sulfate, sodium dodecylsulfate, sodium salts of sulfosuccinates such as sodium dioctylsulfosuccinate, partially esters of fatty acids with alcohols such as glycerine monostearate, partially esters of fatty acids with sorbitans such as sorbitan monolaurate, partially esters of fatty acids with polyhydroxyethylene sorbitans such as polyethyleneglycol sorbitan monolaurate, -monostearate or -monooleate, ethers of fatty alcohols with polyhydroxyethylene, esters of fatty acids with polyhydroxyethylene, copolymers of ethylenoxide and propylenoxide (Pluronic®) and ethoxylated triglycerides. Preference is given to sodium lauryl sulfate.

The amount of the surfactant contained in the pharmaceutical composition of can be from 0 to 5 %, preferably from 0.1 to 2 % by the total weight of the composition.

Film-forming agents and coating materials include, but are not limited to liquid glucose, hydroxy-ethyl cellulose, hydroxypropyl cellulose, hydroxypropyl methylcellulose (hypromellose, HPMC), methylcellulose, ethylcellulose, cellulose acetate phthalate, shellac, polyvinylpyrrolidone, copolymers of vinylpyrrolidone and vinylacetate such as Kollidon® VA64 BASF, copolymers of acrylic- and/or methacrylic acid esters with trimethylammoniummethylacrylate, copolymers of dimethylaminomethacrylic acid and neutral methacrylic acid esters, polymers of methacrylic acid or methacrylic acid esters, copolymers of acrylic acid ethylester and methacrylic acid methyl ester, and copolymers of acrylic acid and acrylic acid methylester. Preference is given to hydroxypropyl methylcellulose (hypromellose, HPMC) as film-forming agent.

Plasticizers include, but are not limited to polyethylene glycol, diethyl phthalate and glycerol. Preference is given to polyethylene glycol.

Coloring agents include, but are not limited to pigments, inorganic pigments, FD&C Red No. 3, FD&C Red No. 20, FD&C Yellow No. 6, FD&C Blue No. 2, D&C Green No. 5, D&C Orange No. 5, D&C Red No. 8, caramel, ferric oxide red, ferric oxide yellow and titanium dioxide. Preference is given to ferric oxide red, ferric oxide yellow and titanium dioxide.

Further commonly used pharmaceutical exipients which can be used as appropriate to formulate the composition for its intended route of administration include, but is not limited to: Acidifying agents for example acetic acid, citric acid, fumaric acid, hydrochloric acid and nitric acid; alkalizing agents for example ammonia solution, ammonium carbonate, diethanolamine, mono-ethanolamine, potassium hydroxide, sodium borate, sodium carbonate, sodium hydroxide, triethanolamine and trolamine; adsorbents for example powdered cellulose and activated charcoal; stabilizers and antioxidants for example ascorbic acid, ascorbyl palmitate, butylated hydroxy-anisole, butylated hydroxytoluene, hypophosphorus acid, monothioglycerol, propyl gallate, sodium ascorbate, sodium bisulfite, sodium formaldehyde sulfoxylate and sodium metabisulfite; other binding materials for example block polymers, natural and synthetic rubber, polyacrylates, polyurethanes, silicones, polysiloxanes and styrene-butadiene copolymers; buffering agents for examples potassium metaphosphate, dipotassium phosphate, sodium acetate, sodium citrate anhydrous and sodium citrate hydrates; encapsulating agents for example gelatin, starch and cellulose derivates); flavornts, masking agents and odors for example anise oil, cinnamon oil, cocoa, menthol, orange oil, peppermint oil and vanillin; humectants for example glycerol, propylene glycol and sorbitol; sweeteners for example aspartame, dextrose, glycerol, mannitol, propylene glycol, saccharin sodium, sorbitol and sucrose; anti-adherents for example magnesium stearate and talc; direct compression excipients for example dibasic calcium phosphate, lactose and microcrystalline cellulose; tablet polishing agents for example carnauba wax and white wax.

Preference is given to a pharmaceutical composition comprising the compound of the formula (I) in a portion of at least 40%, a filler in a portion of from 0 to 60%, a disintegrant in a portion of from 0 to 15%, a binder in a portion of from 0 to 15%, a lubricant in a portion of from 0 to 2% and a surfactant in a portion of from 0 to 5% by weight of the composition.

Also preference is given to a pharmaceutical composition comprising the p-toluenesulfonic acid salt of 4{4-[3-(4-chloro-3-trifluoromethylphenyl)-ureido]-phenoxy}-pyridine-2-carboxylic acid methyl amide in a portion of at least 55%, microcrystalline cellulose as a filler in a portion of from 0 to 60%, croscarmellose sodium as a disintegrant in a portion of from 0 to 15%, hypro-mellose as a binder in a portion of from 0 to 15%, magnesium stearate as a lubricant in a portion of from 0 to 2% and sodium lauryl sulfate as a surfactant in a portion of from 0 to 5% by weight of the composition.

Particular preference is given to a pharmaceutical composition comprising the compound of the formula (I) in a portion of at least 55%, a filler in a portion of from 3 to 20%, a disintegrant in a portion of from 5 to 12%, a binder in a portion of from 0.5 to 8%, a lubricant in a portion of from 0.2 to 0.8% and a surfactant in a portion of from 0.1 to 2% by weight of the composition.

Also particular preference is given to a pharmaceutical composition comprising the p-toluene-sulfonic acid salt of 4{4-[3-(4-chloro-3-trifluoromethylphenyl)-ureido]-phenoxy}-pyridine-2-carboxylic acid methyl amide in a portion of at least 75%, microcrystalline cellulose as a filler in a portion of from 3 to 20%, croscarmellose sodium as a disintegrant in a portion of from 5 to 12%, hypromellose as a binder in a portion of from 0.5 to 8%, magnesium stearate as a lubricant in a portion of from 0.2 to 8% and sodium lauryl sulfate as a surfactant in a portion of from 0.1 to 2% by weight of the composition.

The pharmaceutical composition according to the invention comprising water in an amount of less than or equal to 6%, preferably less than or equal to 3%, more preferably less than or equal to 1.5% by weight of the composition. The water content of the composition is determined by the Karl-Fischer method which is known to a skilled person.

Process for Manufacturing

The present invention also relates to a process for the manufacturing of a solid and oral pharmaceutical composition according to the invention, wherein the compound of formula (I) is blended with at least one pharmaceutically acceptable excipient.

Preference is given to a process for the manufacturing of a solid and oral pharmaceutical composition according to the invention, wherein a) the compound of formula (I) and at least one pharmaceutically acceptable excipient are wet granulated,
b) the granulate is blended with the lubricant and optionally with one or more further pharmaceutically acceptable excipient,
c) the post blend granulate is subdivided into single units,
d) and the product of step c) is optionally coated with one or more further pharmaceutically acceptable excipients.

Step a: Wet Granulation

The compound of formula (I), the filler, preferably microcrystalline cellulose, the binder, preferably hypromellose, the wetting agent, preferably sodium lauryl sulfate and optionally the disintegrant, preferably croscarmellose sodium are granulated in the granulation liquid in terms of a wet granulation. The granulation process is finished when the granulate achieves a "snow ball like consistency". The wet granulation mass is optionally sized and then dried in a suitable device for example in a fluidized bed dryer at an inlet air temperature at a range from 50 to 120° C., preferably from 80 to 100° C. until a residual moisture of less then or equal to 3% preferably then or equal to 1.5% (loss on drying) is reached. The dry granules are optionally sived for example using a sieve size from 1 to 2 mm.

The wet granulation process can be carried out in a high-shear mixer or in a fluidized bed granulator, preferably in a high-shear mixer for wet granulation. The compound of formula (I) can be initially charged as solid in the receiver or is dissolved and/or suspended in the granulation liquid.

Preference is given to a wet granulation process wherein the wetting agent is first dissolved in the granulation liquid and then the blend comprising the compound of formula (I), the filler, the binder and a portion of the disintegrant is added. The blend is mixed before granulation for 1 to 10 minutes, preferably for 1 to 5 minutes.

Alternatively the wetting agent can be added to the dry blend and/or the binder can be dissolved and/or suspended in the granulation liquid.

In the wet granulation process the amount of the granulation liquid is preferably from 40 to 70%, more preferably from 50 to 60% by weight of the dry powder blend.

Preferably the compound of formula (I) is used in the crystalline form, more preferably in a micronized form. The micronized form can have a mean particle size of from 0.5 to 10 μm, preferably from 1 to 6 μm, more preferably from 1 to 3 μm.

The wet granulation mass is preferably sized through a rasp from 2 to 8 mm, preferably from 4 to 6 mm.

Solvents such as granulation liquids and film-coating liquids include, but are not limited to ethanol, acetone, glycerol, isopropanol, purified water and mixtures thereof. Preferably the granulation liquids are purified water, ethanol, acetone or mixtures thereof, more preferably purified water.

Preference is given to a process for the manufacturing of a solid and oral pharmaceutical composition according to the invention, wherein the disintegrant is partly used in the granulation process described under a) and the blending process described under b). More preferably an amount of the disintegrant from 3 to 6% by the total weight of the composition is used in step a) and the remaining is used in step b).

Step b: Blending

The granulate is blended with the lubricant, preferably magnesium stearate and with the remaining disintegrant, preferably croscarmellose sodium, using a suitable device for example a tumbler blender for from 5 to 10 minutes.

Step c: Subdividing/Tablet Compression

The blend is subdivided into single units and further processed to the desired administration form known to the person skilled in the art for example filling into sachets or capsules. Optionally one or more further pharmaceutically acceptable excipients are added. Preferably the blend is subdivided into single units and compressed to tablets using for example a standard rotary tablet press at typical tabletting speeds of 25,000-250,000 tablets/hour.

Step d: Film-coating

The product of step c) is coated with one or more further pharmaceutically acceptable excipients.

Preference is given to a process for the manufacturing of a solid and oral pharmaceutical composition according to the invention, wherein the one or more further pharmaceutically acceptable excipients is selected from the group of plasticizer, film-forming agents and colorants. The plasticizer, preferably polyethylene glycol, the film-forming agent, preferably hypromellose and the colorants, preferably ferric oxide red and/or yellow, are combined with film-coating liquids, preferably purified water to result in a homogeneous coating suspension which is brought up to, preferably sprayed on the product of step c), preferably on the tablets in a suitable coating device for example a perforated drum coater. Other pigments or water soluble dyes or combinations thereof can be used to modify the color of the coating.

Alternative methods for manufacture of a solid oral pharmaceutical composition according to the invention are:

- The compound of formula (I) and at least one pharmaceutically acceptable excipient are blended without granulation and directly compressed to tablets or filled into capsules or sachets. Further excipients may be utilized to result in the formulation. Optionally, the product can be coated with one or more further pharmaceutically acceptable excipients.
- The compound of formula (I) alone or the compound of formula (I) and at least one pharmaceutically acceptable excipient are treated by a dry granulation method and then compressed to tablets or filled into capsules or sachets. Further excipients may be utilized in the formulation. Optionally, the product can be coated with one or more further pharmaceutically acceptable excipients.

Method of Treating Hyper-proliferative Disorders

The present invention also relates to a method for using the pharmaceutical composition according to the invention to treat mammalian hyper-proliferative disorders, including cancer. This method comprises administering the pharmaceutical composition preferably via the oral route to a mammal in need thereof, including a human, an amount which is effective to treat the disorder. The term "hyper-proliferative disorders" and/or "cancer" not only refers to solid tumors, such as cancers of the breast, respiratory tract, brain, reproductive organs, digestive tract, urinary tract, eye, liver, skin, head and neck, thyroid, parathyroid and their distant metastases, but also includes lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, fibrosarcoma, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering the pharmaceutical compositions of the present invention. A patient, for the purpose of this invention, is a mammal, including a human, in need of treatment for the particular condition or disease. Combination therapy The pharmaceutical compositions of this invention can be administered as the sole agent or in combination with one or more other therapies where the combination causes no unacceptable adverse effects. For example, they can be combined with cytotoxic agents, signal transduction inhibitors, or with other anti-cancer agents or therapies, as well as with admixtures and combinations thereof.

In one embodiment, the pharmaceutical compositions of the present invention can be combined with cytotoxic anti-cancer agents. Examples of such agents can be found in the 11th Edition of the Merck Index (1996). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other cytotoxic drugs suitable for use with the pharmaceutical compositions of the invention include, but are not limited to, those compounds acknowledged to be used in the treatment of neoplastic diseases in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxy-uridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compositions of the invention also include newly discovered cytotoxic principles such as oxaliplatin, gemcitabine, capecitabine, epothilone and its natural or synthetic derivatives, temozolomide (Quinn et al., J. Clin. Oncology 2003, 21(4), 646-651), tositumomab (Bexxar), trabedectin (Vidal et al., Proceedings of the American Society for Clinical Oncology 2004, 23, abstract 3181), and the inhibitors of the kinesin spindle protein Eg5 (Wood et al., Curr. Opin. Pharmacol. 2001, 1, 370-377).

In another embodiment, the pharmaceutical compositions of the present invention can be combined with other signal transduction inhibitors. Of particular interest are signal transduction inhibitors which target the EGFR family, such as EGFR, HER-2, and HER4 (Raymond et al., Drugs 2000, 60 (Suppl. 1), 15-23; Harari et al., Oncogene 2000, 19 (53), 6102-6114), and their respective ligands. Examples of such agents include, by no way of limitation, antibody therapies such as Herceptin (trastuzumab), Erbitux (cetuximab), and pertuzumab. Examples of such therapies also include, by no way of limitation, small-molecule kinase inhibitors such as ZD-1839/Iressa (Baselga et al., Drugs 2000, 60 (Suppl. 1), 3340), OSI-774/Tarceva(Pollacketal. J. Pharm. Exp. Ther. 1999, 291(2), 739-748), CI-1033 (Bridges, Curr. Med. Chem. 1999, 6, 825-843), GW-2016 (Lackey et al., 92nd AACR Meeting, New Orleans, Mar. 24-28, 2001, abstract 4582), CP-724,714 (Jani et al., Proceedings of the American Society for Clinical Oncology 2004, 23, abstract 3122), HKI-272 (Rabindran et al., Cancer Res. 2004, 64, 3958-3965), and EKB-569 (Greenberger et al., 11th NCI-EORTC-AACR Symposium on New Drugs in Cancer Therapy, Amsterdam, November 7-10, 2000, abstract 388).

In another embodiment, the pharmaceutical compositions of the present invention can be combined with other signal transduction inhibitors targeting receptor kinases of the split-kinase domain families (VEGFR, FGFR, PDGFR, flt-3, c-kit, c-fms, and the like), and their respective ligands. These agents include, by no way of limitation, antibodies such as Avastin (bevacizumab). These agents also include, by no way of limitation, small-molecule inhibitors such as STI-571/Gleevec (Zvelebil, Curr. Opin. Oncol., Endocr. Metab. Invest. Drugs 2000, 2(1), 74-82), PTK-787 (Wood et al., Cancer Res. 2000, 60(8), 2178-2189), SU-11248 (Demetri et al., Proceedings of the American Society for Clinical Oncology 2004, 23, abstract 3001), ZD-6474 (Hennequin et al., 92nd AACR Meeting, New Orleans, Mar. 24-28, 2001, abstract 3152), AG-13736 (Herbst et al., Clin. Cancer Res. 2003, 9, 16 (suppl 1), abstract C253), KRN-951 (Taguchi et al., 95th AACR Meeting, Orlando, Fla., 2004, abstract 2575), CP-547,632 (Beebe et al., Cancer Res. 2003, 63, 7301-7309), CP-673,451 (Roberts et al., Proceedings of the American Association of Cancer Research 2004, 45, abstract 3989), CHIR-258 (Lee et al., Proceedings of the American Association of Cancer Research 2004, 45, abstract 2130), MLN-518 (Shen et al., Blood 2003, 102, 11, abstract 476), and AZD-2171 (Hennequin et al., Proceedings of the American Association of Cancer Research 2004, 45, abstract 4539).

In another embodiment, the pharmaceutical compositions of the present invention can be combined with inhibitors of the Raf/MEK/ERK transduction pathway (Avruch et al., Recent Prog. Horm. Res. 2001, 56, 127-155), or the PKB (akt) pathway (Lawlor et al., J. Cell Sci. 2001, 114, 2903-2910). These include, by no way of limitation, PD-325901 (Sebolt-Leopold et al., Proceedings of the American Association of Cancer Research 2004, 45, abstract 4003), and ARRY-142886 (Wallace et al., Proceedings of the American Association of Cancer Research 2004, 45, abstract 3891).

In another embodiment, the pharmaceutical compositions of the present invention can be combined with inhibitors of histone deacetylase. Examples of such agents include, by no way of limitation, suberoylanilide hydroxamic acid (SAHA), LAQ-824 (Ottmann et al., Proceedings of the American Society for Clinical Oncology 2004, 23, abstract 3024), LBH-589 (Beck et al., Proceedings of the American Society for Clinical Oncology 2004, 23, abstract 3025), MS-275 (Ryan et al., Proceedings of the American Association of Cancer Research 2004,45, abstract 2452), and FR-901228 (Piekarz et al., Proceedings of the American Society for Clinical Oncology 2004, 23, abstract 3028).

In another embodiment, the pharmaceutical compositions of the present invention can be combined with other anti-cancer agents such as proteasome inhibitors, and m-TOR inhibitors. These include, by no way of limitation, bortezomib (Mackay et al., Proceedings of the American Society for Clinical Oncology 2004, 23, Abstract 3109), and CCI-779 (Wu et al., Proceedings of the American Association of Cancer Research 2004, 45, abstract 3849).

Generally, the use of cytotoxic and/or cytostatic anti-cancer agents in combination with the pharmaceutical compositions of the present invention will serve to:

(1) yield better efficacy in reducing the growth of a tumor or even eliminate the tumor as compared to administration of either agent alone,
(2) provide for the administration of lesser amounts of the administered agents,
(3) provide for a chemotherapeutic treatment protocol that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

It is believed that one skilled in the art, using the preceding information and information available in the art, can utilize the present invention to its fullest extent.

It should be apparent to one of ordinary skill in the art that changes and modifications can be made to this invention without departing from the spirit or scope of the invention as it is set forth herein.

All publications, applications and patents cited above and below are incorporated herein by reference.

The weight data are, unless stated otherwise, percentages by weight and parts are parts by weight.

EXAMPLES

Example 1

Immediate Release Tablet Containing the Tosylate Salt of Compound of Formula (I) and Optionally Subsequent Film-coating 1.1 Composition of tablets containing the p-toluenesulfonic acid salt of 4{4-[3-(4-chloro-3-trifluromethylphenyl)-ureido]-phenoxy}-pyridine-2-carboxylic acid methyl amide (tosylate salt of compound (I))

| Composition [mg/tablet] | Tablet A 50 mg | Tablet B 200 mg | Tablet C 200 mg | Tablet D 400 mg |
|---|---|---|---|---|
| Tablet core: | step a), b) | step a), b), c) ii | Step a), b) c) i | Step a), b) c) i |
| Tosylate salt of compound (I) micronized | 68.5 mg | 274.0 mg | 274.0 mg | 548.0 mg |
| Microcrystalline cellulose | 4.0 mg | 16.0 mg | 16.0 mg | 32.0 mg |
| Croscarmellose sodium | 9.1 mg | 36.4 mg | 36.4 mg | 72.8 mg |
| Hypromellose (5 cP) | 2.55 mg | 10.2 mg | 10.2 mg | 20.4 mg |
| Magnesium stearate | 0.425 mg | 1.7 mg | 2.55 mg[#1] (1.70-2.55 mg) | 5.10 mg |
| Sodium lauryl sulfate | 0.425 mg | 1.7 mg | 1.7 mg | 3.4 mg |
| Weight | 85.0 mg | 340.0 mg | 340.85 mg (340.0-340.85 mg) | 681.70 mg |
| Film-coating: | | | | |
| Opadry Red YS2-15531[#3] | — | 10.0 mg | —[#2]— | —[#2]— |
| Hypromellose (15 cP) | — | — | 6.00 mg (4.8-7.2 mg) | 9.0 mg (7.2-10.8 mg) |
| Macrogol 3350 (polyethylene gycol) | — | — | 2.00 mg (1.6-2.4 mg) | 3.0 mg (2.4-3.6 mg) |
| Titanium dioxide | — | — | 1.73 mg (1.384-2.076 mg) | 1.6 mg (1.28-1.92 mg) |
| Ferric oxide (red) | — | — | 0.27 mg (0.216-0.324 mg) | — |
| Ferric oxide (yellow) | — | — | — | 1.4 mg (1.12-1.68 mg) |
| Weight of film coat | — | 10.0 mg | 10.0 mg (8.0-12.0 mg) | 15.0 mg (12.0-18.0 mg) |
| Total tablet weight | 85.0 mg | 350.0 mg | 350.85 mg (348-352.85 mg) | 696.7 mg (348.0-352.85 mg) |
| Tablet format | Round | round | round | oval |
| Dimensions of the tablet | diameter: 6 mm | diameter: 10 mm, height: 4.5 (±0.3) mm | diameter: 10 mm, height: 4.5 (±0.3) mm | length: 18 mm, width: 8 mm |

[#1]Range for Mg stearate may apply according to manufacturing conditions
[#2]Range for film coat may apply according to manufacturing conditions Fixed ratio of coating components 60% (hypromellose)-20% (polyethylene glycol)-17.3% (titanium dioxide)-2.7% ferric oxide
[#3]Opadry Red YS-15531 ready to use commercial coating system.

1.2 Process for Manufacturing

Step a) Granulation

4{4-[3-(4-chloro-3-trifluoromethylphenyl)-ureido]-phenoxy}-pyridine-2-carboxylic acid methyl amide (tosylate salt of compound (I) micronized, microcrystalline cellulose, croscarmellose sodium, and hypromellose are mixed for 2 minutes in a high shear mixer in order to obtain a powder blend. Sodium lauryl sulfate is dissolved in water. The powder blend is granulated with the solution in a wet granulation process using a high-shear mixer. The granulation process is finished when the granulate achieves a "snow ball like consistency". The wet granulation mass is sized using a 4 mm rasp and then dried in a fluidized bed dryer at an inlet air temperature of 80-100° C. until a residual moisture of 0.3 up to 0.7% by weight (loss on drying) is reached. The dry granules are sieved using a 2 mm sieve size.

Step b) Tablet Compression

The granulate is blended with magnesium stearate and croscarmellose sodium using a tumbler blender for from 5 to 10 minutes. The blend is subdivided into single units and compressed to tablets using a standard rotary tablet press at typical tabletting speeds of from 25,000 to 250,000 tablets/hour.

Step c) Film-Coating

Alternative i:

Hypromellose, polyethylene glycol (Macrogol), titanium dioxide and ferric oxide red are combined with purified water to result in a homogenous coating suspension which is sprayed on the tablets in a perforated drum coater.

Alternative ii:

The commercially available Opadry Red YS-15531 is combined with purified water to result in a homogenous coating suspension which is sprayed on the tablets in a perforated drum coater.

1.3 Properties of the Tablets

TABLE 1

Study of release of compound of formula (I) from tablets B and C
Release of the compound of the formula (I) in % by total weight of the composition.

| | 15 min | 30 min | 45 min | 60 min |
|---|---|---|---|---|
| Tablet B | 94 | 97 | 97 | 97 |
| Tablet C | 96 | 99 | 99 | 99 |

Each value represents the mean of 6 single results. USP apparatus 2, 900 ml 0.1 N HCl+1% Sodium Lauryl Sulfate, 100 rpm The tablets have a stability of more than 18 months (real time stability data) and a hardness of more than 100 N.

The water content of the tablets is less then 1.5% by weight of the composition (determination: Karl-Fischer method)

What is claimed is:

1. A pharmaceutical composition which is a tablet comprising:
   the p-toluenesulfonic acid salt of 4{4-[3-(4-chloro-3-trifluoromethylphenyl)-ureido]-phenoxy}-pyridine-2-carboxylic acid methyl amide as active agent in a portion of at least 55%,
   a filler in a portion of from 3 to 20%,
   a disintegrant in a portion of from 5 to 12%,
   a binder in a portion of from 0.5 to 8.0%,
   a lubricant in a portion of 0.2 to 0.8% and
   a surfactant in a portion of from 0.1 to 2% by weight of the composition.

2. The pharmaceutical composition of claim 1 comprising microcrystalline cellulose as a filler in a portion of from 3 to 20%,
   croscarmellose sodium as a disintegrant in a portion of from 5 to 12%,
   hypromellose as a binder in a portion of from 0.5 to 8.0%,
   magnesium stearate as a lubricant in a portion of from 0.2 to 0.8% and
   sodium lauryl sulfate as a surfactant in a portion of from 0.1 to 2% by weight of the composition.

3. The pharmaceutical composition of claim 1 wherein the composition is a solid oral dosage form.

4. The pharmaceutical composition of claim 1 wherein the composition is an immediate release tablet.

5. The pharmaceutical composition of claim 1 wherein the active agent is micronized.

6. The pharmaceutical composition of claim 5 wherein the micronized form has a mean particle size of from 0.5 to 10 microns.

7. The pharmaceutical composition of claim 1 further comprising water in an amount of less than or equal to 6% by weight of the composition.

8. The pharmaceutical composition according to claim 1 further comprising one or more cytotoxic agents, signal transduction inhibitors, or other anti-cancer agents, as well as with admixtures and combinations thereof.

9. The pharmaceutical composition of claim 1 showing a hardness of more than 80 N.

10. The pharmaceutical composition of claim 1 which is an oval tablet with a longest dimension of less than or equal to 25 mm.

11. The pharmaceutical composition of claim 1 which is a round tablet with a diameter of less than or equal to 13 mm.

12. The pharmaceutical composition of claim 1 wherein the amount of the active ingredient is from 54 mg to 1096 mg.

13. A pharmaceutical composition which is a tablet comprising:
   the p-toluenesulfonic acid salt of 4{4-[3-(4-chloro-3-trifluoromethylphenyl)-ureido]-phenoxy}-pyridine-2-carboxylic acid methyl amide as active agent in a portion of at least 55% a filler in a portion of 3 to 20%, a disintegrant in a portion of 5 to 12% and a binder in a portion of 0.5 to 8.0% by weight of the composition.

14. The pharmaceutical composition of claim 13 wherein the pharmaceutically acceptable excipient comprises microcrystalline cellulose as a filler, croscarmellose sodium as a disintegrant and hypromellose as a binder.

15. The pharmaceutical composition of claim 14 which additionally comprises magnesium stearate as a lubricant in a portion of 0.2 to 0.8%. by weight of the composition.

16. The pharmaceutical composition of claim 15 which additionally comprises sodium lauryl sulfate as a surfactant in a portion of 0.1 to 2% by weight of the composition.

17. The pharmaceutical composition of claim 13 wherein the composition is a solid oral dosage form.

18. The pharmaceutical composition of claim 13 wherein the composition is an immediate release tablet.

19. The pharmaceutical composition of claim 13 wherein the active agent is micronized.

20. The pharmaceutical composition of claim 19 wherein the micronized form has a mean particle size of from 0.5 to 10 microns.

21. The pharmaceutical composition of claim 13 further comprising water in an amount of less than or equal to 6%.

22. The pharmaceutical composition according to claim 13 further comprising one or more cytotoxic agents, signal transduction inhibitors, or other anti-cancer agents, as well as with admixtures and combinations thereof.

23. The pharmaceutical composition of claim 13 which is an oval tablet with a longest dimension of less than or equal to 25 mm.

24. The pharmaceutical composition of claim 13 which is a round tablet with a diameter of less than or equal to 13 mm.

25. The pharmaceutical composition of claim 13 wherein the amount of the active ingredient is from 54 mg to 1096 mg.

26. The pharmaceutical composition of claim 13 which additionally comprises a lubricant in a portion of 0.2 to 0.8% by weight of the composition and optionally a surfactant in a portion of 0.1 to 2% by weight of the composition.

27. A process for manufacturing the pharmaceutical composition according to claim 13 wherein the active agent is blended with at least one pharmaceutically acceptable excipient which is a filler, a disintegrant, a binder, a lubricant or a surfactant.

28. The process of claim 27 wherein:
   a) the active agent and at least one pharmaceutically acceptable excipient are wet granulated;
   b) the granulate is blended with the lubricant and optionally with one or more further pharmaceutically acceptable excipient;
   c) the post blend granulate is subdivided into single units and
   d) the product of step c) is optionally coated with one or more further pharmaceutically acceptable excipients.

29. The process of claim 28 wherein the product of step c) is coated with one or more further pharmaceutically acceptable excipients.

30. The process of claim 27 wherein the active agent and at least one pharmaceutically acceptable excipient are blended without granulation and directly compressed to tablets.

31. The process of claim 27 wherein the active agent alone or the active agent and at least one pharmaceutically acceptable excipient are treated by a dry granulation method and then compressed to tablets.

32. A method for treating a mammalian hyper-proliferative disorder comprising administering a therapeutically effective amount of the pharmaceutical composition of claim 13 to a mammal in need thereof.

33. A pharmaceutical composition which is an immediate release tablet comprising:
   the p-toluenesulfonic acid salt of 4{4-[3-(4-chloro-3-trifluoromethylphenyl)-ureido]-phenoxy}-pyridine-2-carboxylic acid methyl amide as active agent in a portion of at least 55% and a pharmaceutically acceptable excipient which comprises a filler, a disintegrant, a binder and a lubricant, wherein one or more of the following applies, said filler is in a portion of 3 to 20%, said disintegrant is in a portion of 5 to 12%, said binder is in a portion of 0.5 to 8.0%, or said lubricant is in a portion of 0.2 to 0.8% by weight of the composition.

34. The pharmaceutical composition of claim 33 which additionally comprises a surfactant in a portion of 0.1 to 2% by weight of the composition.

35. A pharmaceutical composition which is an immediate release tablet comprising:
the p-toluenesulfonic acid salt of 4{4-[3-(4-chloro-3-trifluoromethylphenyl)-ureido]-phenoxy}-pyridine-2-carboxylic acid methyl amide as active agent in a portion of at least 55% and at least one pharmaceutically acceptable excipient wherein the pharmaceutically acceptable excipient comprises microcrystalline cellulose as a filler in a portion of 3 to 20% by weight of the composition, croscarmellose sodium as a disintegrant in a portion of 5 to 12% by weight of the composition, hypromellose as a binder in a portion of 0.5 to 8.0% by weight of the composition, or magnesium stearate as a lubricant in a portion of 0.2 to 0.8% by weight of the composition.

36. The pharmaceutical composition of claim 35 which additionally comprises sodium lauryl sulfate as a surfactant in a portion of 0.1 to 2% by weight of the composition.

37. A pharmaceutical composition which is an immediate release tablet -showing a hardness of more than 80 N comprising:
the p-toluenesulfonic acid salt of 4{4-[3-(4-chloro-3-trifluoromethylphenyl)-ureido]-phenoxy}-pyridine-2-carboxylic acid methyl amide as active agent in a portion of at least 55% and at least one pharmaceutically acceptable excipient which is a filler in a portion of 3 to 20%, a disintegrant in a portion of 5 to 12%, a binder in a portion of 0.5 to 8.0%, a lubricant in a portion of 0.2 to 0.8% or a surfactant in a portion of 0.1 to 2% by weight of the composition.

38. A pharmaceutical composition which is an immediate release tablet comprising:
the p-toluenesulfonic acid salt of 4{4-[3-(4-chloro-3-trifluoromethylphenyl)-ureido]-phenoxy}-pyridine-2-carboxylic acid methyl amide as active agent in a portion of at least 55% and on microcrystalline cellulose as filler in a portion of 3 to 20% by weight of the composition.

39. The pharmaceutical composition of claim 38 which additionally comprises crosscarmellose sodium as a disintegrant, and magnesium stearate as a lubricant.

40. An immediate release pharmaceutical composition comprising the active agent the p-toluenesulfonic acid salt of 4{4-[3-(4-chloro-3-trifluoromethylphenyl)-ureido]-phenoxy}-pyridine-2-carboxylic acid methyl amide in a portion of at least 40% by weight of the composition and at least one pharmaceutically acceptable excipient, wherein the pharmaceutical composition is an immediate release tablet.

41. The immediate release pharmaceutical composition of claim 40 comprising the active agent in a portion of at least 55% by weight of the composition.

42. The immediate release pharmaceutical composition of claim 40 comprising the active agent in a portion of at least 75% by weight of the composition.

43. The immediate release pharmaceutical composition of claim 40 wherein the active agent, the p-toluenesulfonic acid salt of 4{4-[3-(4-chloro-3-trifluoromethylphenyl)-ureido]-phenoxy}-pyridine-2-carboxylic acid methyl amide, is present in an amount of about 274 mg.

44. The immediate release pharmaceutical composition of claim 40 showing a hardness of more than 80 N.

45. The immediate release pharmaceutical composition of claim 43 showing a hardness of more than 80 N.

46. The immediate release pharmaceutical composition of claim 43 showing a hardness of more than 100 N.

47. The immediate release pharmaceutical composition of claim 40 which is an oval tablet with a longest dimension of less than or equal to 25 mm or a round tablet with a diameter of less than or equal to 13 mm.

48. The immediate release pharmaceutical composition of claim 43 which is an oval tablet with a longest dimension of less than or equal to 25 mm or a round tablet with a diameter of less than or equal to 13 mm.

49. The immediate release pharmaceutical composition of claim 44 which is an oval tablet with a longest dimension of less than or equal to 25 mm or a round tablet with a diameter of less than or equal to 13 mm.

50. The immediate release pharmaceutical composition of claim 45 which is an oval tablet with a longest dimension of less than or equal to 25 mm or a round tablet with a diameter of less than or equal to 13 mm.

51. The immediate release pharmaceutical composition of claim 46 which is an oval tablet with a longest dimension of less than or equal to 25 mm or a round tablet with a diameter of less than or equal to 13 mm.

52. The immediate release pharmaceutical composition of claim 40 wherein the at least one pharmaceutically acceptable excipient is one or more of microcrystalline cellulose, croscarmellose sodium, hypromellose, magnesium stearate or sodium lauryl sulfate.

53. The immediate release pharmaceutical composition of claim 43 wherein the at least one pharmaceutically acceptable excipient is one or more of microcrystalline cellulose, croscarmellose sodium, hypromellose, magnesium stearate or sodium lauryl sulfate.

54. The immediate release pharmaceutical composition of claim 40 wherein the at least one pharmaceutically acceptable excipient is one or more of a filler, disintegrant, binder, lubricant or surfactant.

55. The immediate release pharmaceutical composition of claim 43 wherein the at least one pharmaceutically acceptable excipient is one or more of a filler, disintegrant, binder, lubricant or surfactant.

56. The immediate release pharmaceutical composition of claim 55 comprising filler in a portion of from 3 to 20% by weight of the composition.

57. The immediate release pharmaceutical composition of claim 56 comprising microcrystalline cellulose as filler.

58. The immediate release pharmaceutical composition of claim 55 comprising disintegrant in a portion of from 5 to 12% by weight of the composition.

59. The immediate release pharmaceutical composition of claim 58 comprising croscarmellose sodium as disintegrant.

60. The immediate release pharmaceutical composition of claim 55 comprising binder in a portion of from 0.5 to 8.0% by weight of the composition.

61. The immediate release pharmaceutical composition of claim 60 comprising hypromellose as binder.

62. The immediate release pharmaceutical composition of claim 55 comprising lubricant in a portion of from 0.2 to 0.8% by weight of the composition as an excipient.

63. The immediate release pharmaceutical composition of claim 62 comprising magnesium stearate as lubricant.

64. The immediate release pharmaceutical composition of claim 55 comprising surfactant in a portion of from 0.1 to 2% by weight of the composition as an excipient.

65. The immediate release pharmaceutical composition of claim 64 comprising sodium lauryl sulfate as surfactant.

66. The immediate release pharmaceutical composition of claim 43 comprising a filler, disintegrant, binder and lubricant as excipients.

67. The immediate release pharmaceutical composition of claim 45 comprising a filler, disintegrant, binder and lubricant as excipients.

68. The immediate release pharmaceutical composition of claim 50 comprising a filler, disintegrant, binder and lubricant as excipients.

69. The immediate release pharmaceutical composition of claim 53 comprising a filler, disintegrant, binder and lubricant as excipients.

70. The immediate release pharmaceutical composition of claim 41 wherein the active agent, the p-toluenesulfonic acid salt of 4{4-[3-(4-chloro-3-trifluoromethylphenyl)-ureido]-phenoxy}-pyridine-2-carboxylic acid methyl amide, is present in an amount of about 274 mg.

71. The immediate release pharmaceutical composition of claim 70 showing a hardness of more than 80 N.

72. The immediate release pharmaceutical composition of claim 70 showing a hardness of more than 100 N.

73. The immediate release pharmaceutical composition of claim 70 which is an oval tablet with a longest dimension of less than or equal to 25 mm or a round tablet with a diameter of less than or equal to 13 mm.

74. The immediate release pharmaceutical composition of claim 71 which is an oval tablet with a longest dimension of less than or equal to 25 mm or a round tablet with a diameter of less than or equal to 13 mm.

75. The immediate release pharmaceutical composition of claim 42 wherein the active agent, the p-toluenesulfonic acid salt of 4{4-[3-(4-chloro-3-trifluoromethylphenyl)-ureido]-phenoxy}-pyridine-2-carboxylic acid methyl amide, is present in an amount of about 274 mg.

76. The immediate release pharmaceutical composition of claim 75 showing a hardness of more than 80 N.

77. The immediate release pharmaceutical composition of claim 75 showing a hardness of more than 100 N.

78. The immediate release pharmaceutical composition of claim 75 which is an oval tablet with a longest dimension of less than or equal to 25 mm or a round tablet with a diameter of less than or equal to 13 mm.

79. The immediate release pharmaceutical composition of claim 76 which is an oval tablet with a longest dimension of less than or equal to 25 mm or a round tablet with a diameter of less than or equal to 13 mm.

80. An immediate release pharmaceutical composition comprising the active agent p-toluenesulfonic acid salt of 4{4-[3-(4-chloro-3-trifluoromethylphenyl)-ureido]-phenoxy}-pyridine-2-carboxylic acid methyl amide in an amount of about 274 mg and at least one pharmaceutically acceptable excipient wherein the pharmaceutical composition is an immediate release tablet showing a hardness of more than 80 N, which is either an oval tablet with a longest dimension of less than or equal to 25 mm or a round tablet with a diameter of less than or equal to 13 mm.

81. The immediate release pharmaceutical composition of claim 80 showing a hardness of more than 100 N.

82. The immediate release pharmaceutical composition of claim 80 wherein the at least one pharmaceutically acceptable excipient is one or more of microcrystalline cellulose, croscarmellose sodium, hypromellose, magnesium stearate or sodium lauryl sulfate.

83. The immediate release pharmaceutical composition of claim 80 wherein the at least one pharmaceutically acceptable excipient is one or more of a filler, disintegrant, binder, lubricant or surfactant.

84. The immediate release pharmaceutical composition of claim 72 which is an oval tablet with a longest dimension of less than or equal to 25 mm or a round tablet with a diameter of less than or equal to 13 mm.

85. The immediate release pharmaceutical composition of claim 77 which is an oval tablet with a longest dimension of less than or equal to 25 mm or a round tablet with a diameter of less than or equal to 13 mm.

86. The immediate release pharmaceutical composition of claim 40 showing a hardness of more than 100 N.

87. The immediate release pharmaceutical composition of claim 86 which is an oval tablet with a longest dimension of less than or equal to 25 mm or a round tablet with a diameter of less than or equal to 13 mm.

88. The immediate release pharmaceutical composition of claim 41 showing a hardness of more than 80 N.

89. The immediate release pharmaceutical composition of claim 41 showing a hardness of more than 100 N.

90. The immediate release pharmaceutical composition of claim 41 which is an oval tablet with a longest dimension of less than or equal to 25 mm or a round tablet with a diameter of less than or equal to 13 mm.

91. The immediate release pharmaceutical composition of claim 88 which is an oval tablet with a longest dimension of less than or equal to 25 mm or a round tablet with a diameter of less than or equal to 13 mm.

92. The immediate release pharmaceutical composition of claim 42 showing a hardness of more than 80 N.

93. The immediate release pharmaceutical composition of claim 42 showing a hardness of more than 100 N.

94. The immediate release pharmaceutical composition of claim 42 which is an oval tablet with a longest dimension of less than or equal to 25 mm or a round tablet with a diameter of less than or equal to 13 mm.

95. The immediate release pharmaceutical composition of claim 92 which is an oval tablet with a longest dimension of less than or equal to 25 mm or a round tablet with a diameter of less than or equal to 13 mm.

96. The immediate release pharmaceutical composition of claim 93 which is an oval tablet with a longest dimension of less than or equal to 25 mm or a round tablet with a diameter of less than or equal to 13 mm.

97. The immediate release pharmaceutical composition of claim 41 wherein the at least one pharmaceutically acceptable excipient is one or more of microcrystalline cellulose, croscarmellose sodium, hypromellose, magnesium stearate or sodium lauryl sulfate.

98. The immediate release pharmaceutical composition of claim 42 wherein the at least one pharmaceutically acceptable excipient is one or more of microcrystalline cellulose, croscarmellose sodium, hypromellose, magnesium stearate or sodium lauryl sulfate.

99. The immediate release pharmaceutical composition of claim 41 wherein the at least one pharmaceutically acceptable excipient is one or more of a filler, disintegrant, binder, lubricant or surfactant.

100. The immediate release pharmaceutical composition of claim 42 wherein the at least one pharmaceutically acceptable excipient is one or more of a filler, disintegrant, binder, lubricant or surfactant.

101. The immediate release pharmaceutical composition of claim 40 comprising a filler, disintegrant, binder and lubricant as excipients.

102. The immediate release pharmaceutical composition of claim 41 comprising a filler, disintegrant, binder and lubricant as excipients.

103. The immediate release pharmaceutical composition of claim 42 comprising a filler, disintegrant, binder and lubricant as excipients.

\* \* \* \* \*